(12) United States Patent
Schneider et al.

(10) Patent No.: US 9,039,855 B2
(45) Date of Patent: May 26, 2015

(54) APPARATUSES AND METHODS FOR MAKING ABSORBENT ARTICLES

(75) Inventors: Uwe Schneider, Cincinnati, OH (US); Gary Dean LaVon, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/435,036

(22) Filed: Mar. 30, 2012

(65) Prior Publication Data

US 2013/0255862 A1    Oct. 3, 2013

(51) Int. Cl.
| | |
|---|---|
| *B32B 38/04* | (2006.01) |
| *B32B 37/02* | (2006.01) |
| *B32B 37/12* | (2006.01) |
| *B32B 38/10* | (2006.01) |
| *A61F 13/00* | (2006.01) |
| *A61F 13/15* | (2006.01) |

(52) U.S. Cl.
CPC ..... *A61F 13/15593* (2013.01); *A61F 13/15723* (2013.01); *A61F 13/15739* (2013.01)

(58) Field of Classification Search
CPC .............. A61F 13/15593; A61F 13/15739; A61F 13/15723
USPC ............ 156/161, 227, 73.1, 204; 604/385.27, 604/385.24, 385.26
See application file for complete search history.

(56) References Cited

U.S. PATENT DOCUMENTS

| | | |
|---|---|---|
| 167,309 A | 8/1875 | Daniels |
| 1,351,751 A | 9/1920 | Hoff |
| 3,083,757 A | 4/1963 | Kraft et al. |
| 3,340,757 A | 9/1967 | Rudszinat |
| 3,736,659 A | 6/1973 | McLean |
| 3,753,397 A | 8/1973 | Shrewsbury et al. |

(Continued)

FOREIGN PATENT DOCUMENTS

| | | |
|---|---|---|
| CA | 2152328 C | 8/1996 |
| EP | 0 487 921 A2 | 6/1992 |

(Continued)

OTHER PUBLICATIONS

U.S. Appl. No. 13/434,984, filed Mar. 30, 2012—Office Action mailed Dec. 21, 2012, (7 pages).

(Continued)

*Primary Examiner* — Jeff Aftergut
*Assistant Examiner* — Marta Dulko
(74) *Attorney, Agent, or Firm* — Charles R. Matson

(57) ABSTRACT

The present disclosure relates to methods and apparatuses for assembling diapers, each including a chassis connected with front and back elastic belts. As discussed in more detail below, opposing end regions of the chassis are connected with regions of the elastic belts where the elasticity of the elastic belts has been removed or deactivated. An elastic laminate may be formed by continuously bonding elastic strands between a first continuous substrate layer and a second continuous substrate layer such that the elastic strands are bonded to both the first substrate layer and the second substrate layer in heavy-bond regions. And the elastic strands are bonded to the first substrate layer and/or the second substrate layer with in light-bond regions. The elastic strands are then intermittently deactivated by cutting the strands into one or more discrete pieces in the light-bond regions. The discrete pieces retract and remain in the light-bond regions.

6 Claims, 21 Drawing Sheets

(56) References Cited

U.S. PATENT DOCUMENTS

| | | |
|---|---|---|
| 3,821,837 A | 7/1974 | Faber |
| 3,823,634 A | 7/1974 | Rod et al. |
| 3,828,637 A | 8/1974 | Slack |
| 3,835,746 A | 9/1974 | Young, Jr. et al. |
| 3,848,594 A | 11/1974 | Buell |
| 3,850,059 A | 11/1974 | Kang |
| 3,860,003 A | 1/1975 | Buell |
| 3,957,569 A | 5/1976 | Freitag |
| 4,020,724 A | 5/1977 | Quinlan |
| 4,068,694 A | 1/1978 | Schmidt et al. |
| 4,081,301 A | 3/1978 | Buell |
| 4,284,454 A | 8/1981 | Joa |
| 4,347,959 A | 9/1982 | Ivinger |
| 4,353,762 A | 10/1982 | Bouda |
| 4,425,173 A | 1/1984 | Frick |
| 4,479,836 A | 10/1984 | Dickover et al. |
| 4,483,228 A | 11/1984 | Waite et al. |
| 4,561,355 A | 12/1985 | Cuir et al. |
| 4,610,678 A | 9/1986 | Weisman et al. |
| 4,617,082 A | 10/1986 | Oshefsky et al. |
| 4,634,482 A | 1/1987 | Lammers |
| 4,640,165 A | 2/1987 | McMahon et al. |
| 4,658,875 A | 4/1987 | Grabovac |
| 4,662,875 A | 5/1987 | Hirotsu et al. |
| 4,673,402 A | 6/1987 | Weisman et al. |
| 4,695,278 A | 9/1987 | Lawson |
| 4,699,033 A | 10/1987 | Gherardi |
| 4,699,622 A | 10/1987 | Toussant et al. |
| 4,704,115 A | 11/1987 | Buell |
| 4,743,144 A | 5/1988 | Shikata |
| 4,785,697 A | 11/1988 | Gherardi |
| 4,795,454 A | 1/1989 | Dragoo |
| 4,826,090 A | 5/1989 | Orphall |
| 4,834,735 A | 5/1989 | Alemany et al. |
| 4,846,815 A | 7/1989 | Scripps |
| 4,888,231 A | 12/1989 | Angstadt |
| 4,894,060 A | 1/1990 | Nestegard |
| 4,900,384 A | 2/1990 | Sanders et al. |
| 4,909,803 A | 3/1990 | Aziz et al. |
| 4,919,738 A | 4/1990 | Ball et al. |
| 4,920,843 A | 5/1990 | Strömberg et al. |
| 4,946,527 A | 8/1990 | Battrell |
| 4,962,683 A | 10/1990 | Scheffer et al. |
| 4,963,140 A | 10/1990 | Robertson et al. |
| 5,032,120 A | 7/1991 | Freeland et al. |
| 5,046,671 A | 9/1991 | Hughes |
| 5,064,489 A | 11/1991 | Ujimoto et al. |
| 5,086,683 A | 2/1992 | Steidinger |
| 5,137,537 A | 8/1992 | Herron et al. |
| 5,147,345 A | 9/1992 | Young et al. |
| 5,151,092 A | 9/1992 | Buell et al. |
| 5,156,793 A | 10/1992 | Buell et al. |
| 5,167,897 A | 12/1992 | Weber et al. |
| 5,221,274 A | 6/1993 | Buell et al. |
| 5,224,408 A | 7/1993 | Steidinger |
| 5,242,436 A | 9/1993 | Weil et al. |
| 5,260,345 A | 11/1993 | DesMarais et al. |
| 5,271,442 A | 12/1993 | Carpenter et al. |
| 5,327,804 A | 7/1994 | Creaden |
| 5,342,338 A | 8/1994 | Roe |
| 5,357,836 A | 10/1994 | Strömberg et al. |
| 5,363,728 A | 11/1994 | Elsner et al. |
| 5,387,207 A | 2/1995 | Dyer et al. |
| 5,388,490 A | 2/1995 | Buck |
| 5,393,360 A | 2/1995 | Bridges et al. |
| 5,397,316 A | 3/1995 | LaVon et al. |
| 5,409,442 A | 4/1995 | Smithwick, Jr. |
| 5,499,978 A | 3/1996 | Buell et al. |
| 5,500,075 A | 3/1996 | Herrmann |
| 5,507,736 A | 4/1996 | Clear et al. |
| 5,525,175 A | 6/1996 | Blenke et al. |
| 5,554,145 A | 9/1996 | Roe et al. |
| 5,562,646 A | 10/1996 | Goldman et al. |
| 5,569,234 A | 10/1996 | Buell et al. |
| 5,580,411 A | 12/1996 | Nease et al. |
| 5,591,152 A | 1/1997 | Buell et al. |
| 5,599,335 A | 2/1997 | Goldman et al. |
| 5,622,581 A | 4/1997 | Ducker et al. |
| 5,625,222 A | 4/1997 | Yoeda et al. |
| 5,628,097 A | 5/1997 | Benson et al. |
| 5,643,396 A | 7/1997 | Rajala et al. |
| 5,660,657 A | 8/1997 | Rajala et al. |
| 5,669,894 A | 9/1997 | Goldman et al. |
| 5,671,589 A | 9/1997 | Irvine et al. |
| 5,683,531 A | 11/1997 | Roessler et al. |
| 5,702,551 A | 12/1997 | Huber et al. |
| 5,707,330 A | 1/1998 | Kiamco et al. |
| 5,709,255 A | 1/1998 | Toogood |
| 5,745,922 A | 5/1998 | Rajala et al. |
| 5,775,194 A | 7/1998 | Spada |
| 5,916,661 A | 6/1999 | Benson et al. |
| 6,004,306 A | 12/1999 | Robles et al. |
| 6,026,727 A | 2/2000 | Meeks |
| 6,107,539 A | 8/2000 | Palumbo et al. |
| 6,120,487 A | 9/2000 | Ashton |
| 6,131,627 A | 10/2000 | Zaiser |
| 6,217,690 B1 | 4/2001 | Rajala et al. |
| 6,235,137 B1 | 5/2001 | Van Eperen et al. |
| 6,248,097 B1 | 6/2001 | Beitz et al. |
| 6,248,195 B1 | 6/2001 | Schmitz |
| 6,279,444 B1 | 8/2001 | Kellner et al. |
| 6,319,347 B1 | 11/2001 | Rajala et al. |
| 6,432,098 B1 | 8/2002 | Kline et al. |
| 6,460,439 B2 | 10/2002 | Belanger |
| 6,481,318 B1 | 11/2002 | Kinigakis et al. |
| 6,482,278 B1 | 11/2002 | McCabe et al. |
| 6,545,197 B1 | 4/2003 | Muller et al. |
| 6,546,987 B1 | 4/2003 | Tachibana et al. |
| 6,554,815 B1 | 4/2003 | Umebayashi |
| 6,602,374 B2 | 8/2003 | Gunther et al. |
| 6,641,692 B2 | 11/2003 | Reynolds et al. |
| 6,705,981 B2 | 3/2004 | Bergeron et al. |
| 6,711,824 B2 | 3/2004 | Hruska |
| 6,790,798 B1 | 9/2004 | Suzuki et al. |
| 6,811,019 B2 | 11/2004 | Christian et al. |
| 7,001,477 B2 | 2/2006 | Saraf |
| 7,171,884 B2 | 2/2007 | De Torre |
| 7,171,885 B1 | 2/2007 | Obiol |
| 7,189,031 B2 | 3/2007 | Bellinger et al. |
| 7,192,422 B2 | 3/2007 | Otsubo |
| 7,214,175 B2 | 5/2007 | Janzen |
| 7,220,251 B2 | 5/2007 | Otsubo et al. |
| 7,329,245 B2 | 2/2008 | Torigoshi et al. |
| 7,383,865 B2 | 6/2008 | Umebayashi et al. |
| 7,435,245 B2 | 10/2008 | Wendelstorf et al. |
| 7,435,309 B2 | 10/2008 | Komatsu |
| 7,530,972 B2 | 5/2009 | Ando et al. |
| 7,569,039 B2 | 8/2009 | Matsuda et al. |
| 7,587,966 B2 | 9/2009 | Nakakado et al. |
| 7,708,849 B2 | 5/2010 | McCabe |
| 7,713,371 B2 | 5/2010 | Lohrengel et al. |
| 7,771,407 B2 | 8/2010 | Umebayashi |
| 7,777,094 B2 | 8/2010 | Mori et al. |
| 7,832,435 B1 | 11/2010 | Liu |
| 7,861,756 B2 * | 1/2011 | Jenquin et al. ................. 156/496 |
| 7,900,542 B2 | 3/2011 | Kapolnek |
| 7,954,681 B2 | 6/2011 | Smith et al. |
| 8,092,440 B2 | 1/2012 | Hermansson et al. |
| 8,142,590 B2 | 3/2012 | Rajala et al. |
| 8,196,500 B2 | 6/2012 | Mansfield et al. |
| 8,312,797 B2 | 11/2012 | Hsu |
| 2001/0023343 A1 | 9/2001 | Mizutani et al. |
| 2002/0046802 A1 | 4/2002 | Tachibana et al. |
| 2002/0173764 A1 | 11/2002 | Takino et al. |
| 2002/0184985 A1 | 12/2002 | Ishibuchi et al. |
| 2003/0089447 A1 * | 5/2003 | Molee et al. ................. 156/161 |
| 2003/0135189 A1 * | 7/2003 | Umebayashi ............ 604/385.27 |
| 2004/0035521 A1 | 2/2004 | Nakakado et al. |
| 2004/0097895 A1 | 5/2004 | Busam et al. |
| 2004/0158212 A1 | 8/2004 | Ponomenko et al. |
| 2004/0158217 A1 | 8/2004 | Wu et al. |
| 2004/0243083 A1 * | 12/2004 | Matsuda et al. ......... 604/385.01 |
| 2005/0107764 A1 | 5/2005 | Matsuda et al. |
| 2005/0230037 A1 | 10/2005 | Jenquin et al. |

(56) References Cited

U.S. PATENT DOCUMENTS

| | | | |
|---|---|---|---|
| 2007/0157778 A1 | 7/2007 | Lohrengel et al. | |
| 2007/0246152 A1 | 10/2007 | Chang et al. | |
| 2008/0028902 A1 | 2/2008 | Baggot et al. | |
| 2009/0145276 A1 | 6/2009 | Scheck et al. | |
| 2009/0283207 A1 | 11/2009 | Tachibana et al. | |
| 2009/0312730 A1 | 12/2009 | LaVon et al. | |
| 2010/0101392 A1 | 4/2010 | Zeuschner | |
| 2010/0167896 A1 | 7/2010 | Hada et al. | |
| 2010/0221496 A1* | 9/2010 | de Jong | 428/172 |
| 2010/0252178 A1 | 10/2010 | Takino et al. | |
| 2010/0305532 A1 | 12/2010 | Ashton et al. | |
| 2011/0125122 A1 | 5/2011 | Thorson et al. | |
| 2011/0313387 A1 | 12/2011 | Ashton et al. | |
| 2012/0021186 A1 | 1/2012 | Schneider | |
| 2012/0061015 A1 | 3/2012 | LaVon et al. | |
| 2012/0061016 A1 | 3/2012 | LaVon et al. | |
| 2012/0086145 A1 | 4/2012 | Nakamura et al. | |
| 2012/0095429 A1* | 4/2012 | Kobayashi et al. | 604/385.16 |
| 2012/0247681 A1 | 10/2012 | Yamamoto | |
| 2012/0258277 A1* | 10/2012 | Ukegawa | 428/114 |
| 2013/0306151 A1 | 11/2013 | Nustonen et al. | |

FOREIGN PATENT DOCUMENTS

| | | | |
|---|---|---|---|
| EP | 0 626 161 | A1 | 11/1994 |
| EP | 1 188 427 | B1 | 3/1999 |
| EP | 1 078 620 | A2 | 2/2000 |
| EP | 1 260 206 | B1 | 6/2005 |
| EP | 1 961 404 | B1 | 8/2008 |
| EP | 2 415 430 | A1 | 2/2012 |
| GB | 2 106 441 | A | 4/1983 |
| JP | 63-116293 | U | 1/1987 |
| JP | 63-144995 | | 9/1988 |
| JP | 09-299398 | A | 11/1997 |
| JP | 11-347988 | | 12/1999 |
| JP | 3545210 | B | 1/2000 |
| JP | 4090158 | B | 3/2001 |
| JP | 2001-121471 | | 5/2001 |
| JP | 2009-172231 | A | 8/2006 |
| JP | 4630352 | B | 8/2008 |
| JP | 2008-229006 | A | 10/2008 |
| JP | 2008-229007 | A | 10/2008 |

OTHER PUBLICATIONS

U.S. Appl. No. 13/435,063, filed Mar. 30, 2012—Office Action mailed Jan. 3, 2013, (8 pages).
U.S. Appl. No. 13/435,247, filed Mar. 30, 2012—Office Action mailed Jan. 4, 2013, (9 pages).
U.S. Appl. No. 13/434,912, filed Mar. 30, 2012—Office Action mailed Dec. 4, 2012, (16 pages).
U.S. Appl. No. 13/435,503, filed Mar. 30, 2012—Office Action mailed Jan. 10, 2013, (5 pages).
International Search Report, PCT/US2013032736 dated Jun. 11, 2013, 9 pages.

* cited by examiner

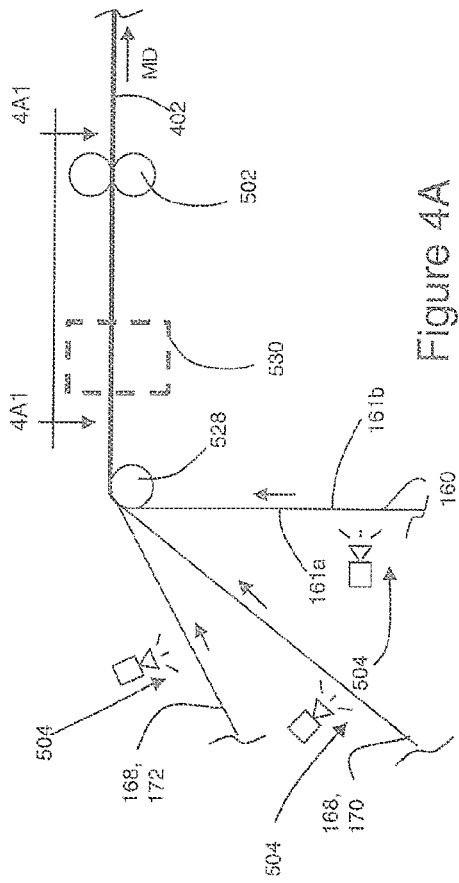
Figure 4A
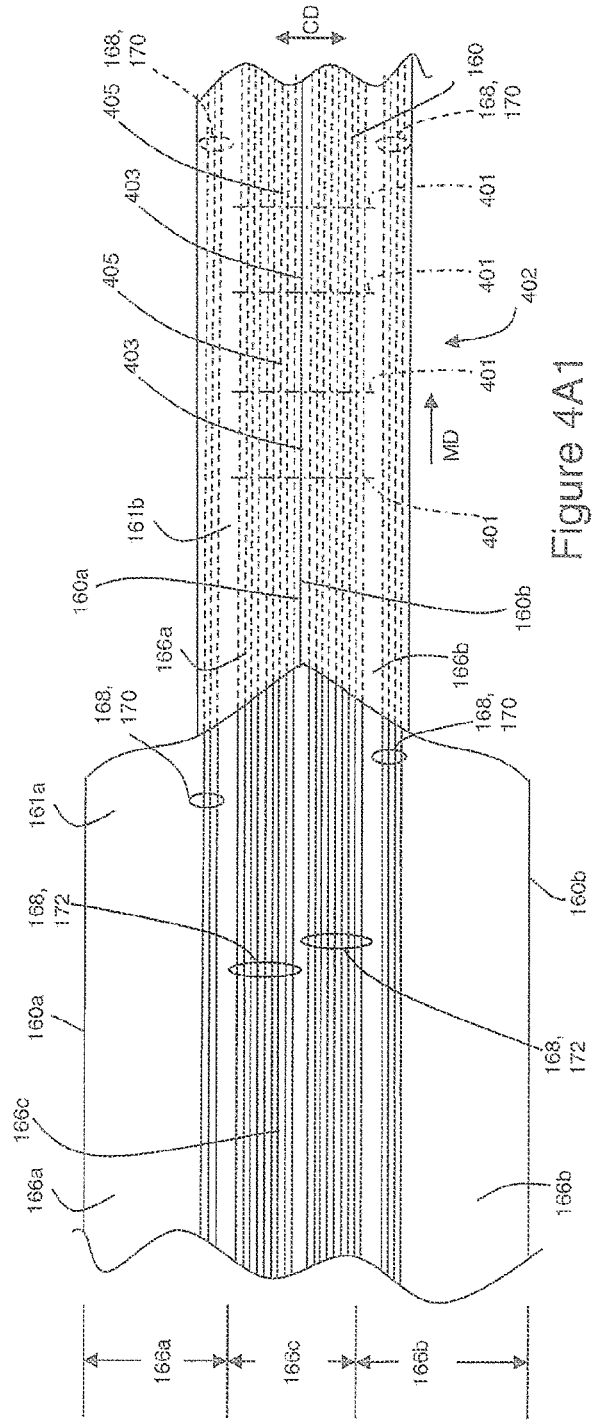
Figure 4A1

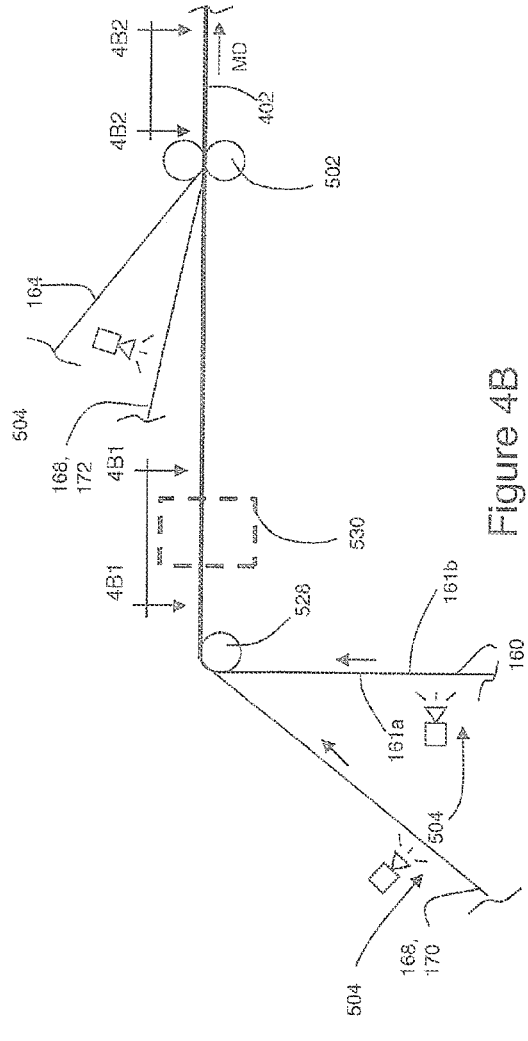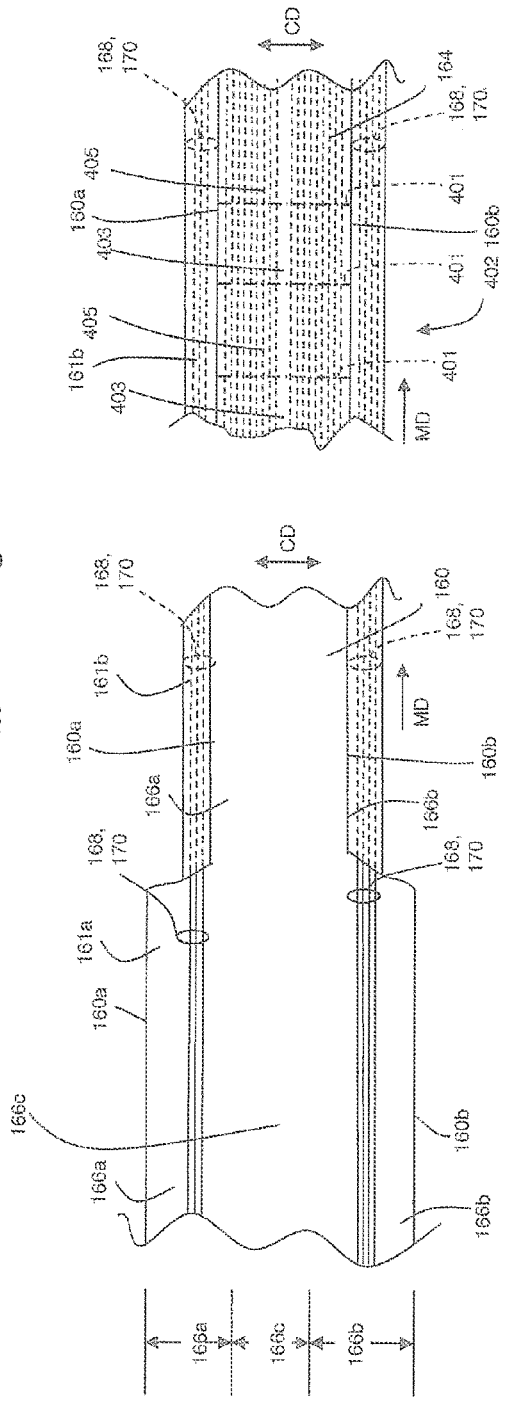

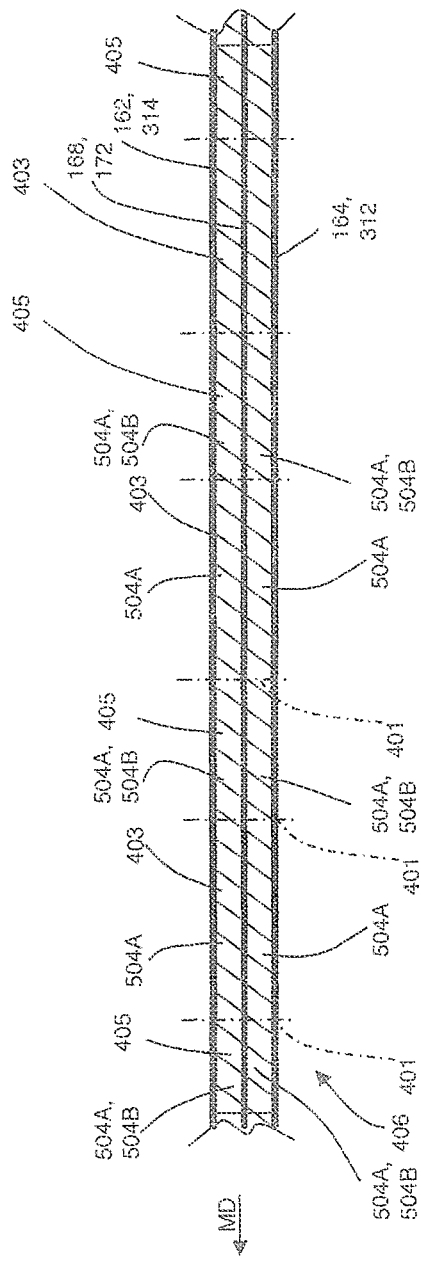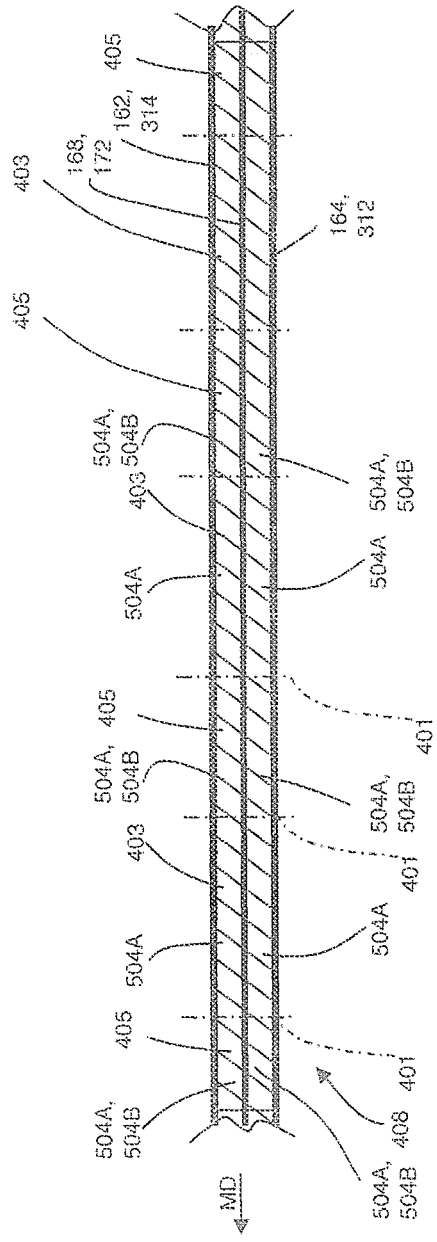
Figure 5B1
Figure 5B2

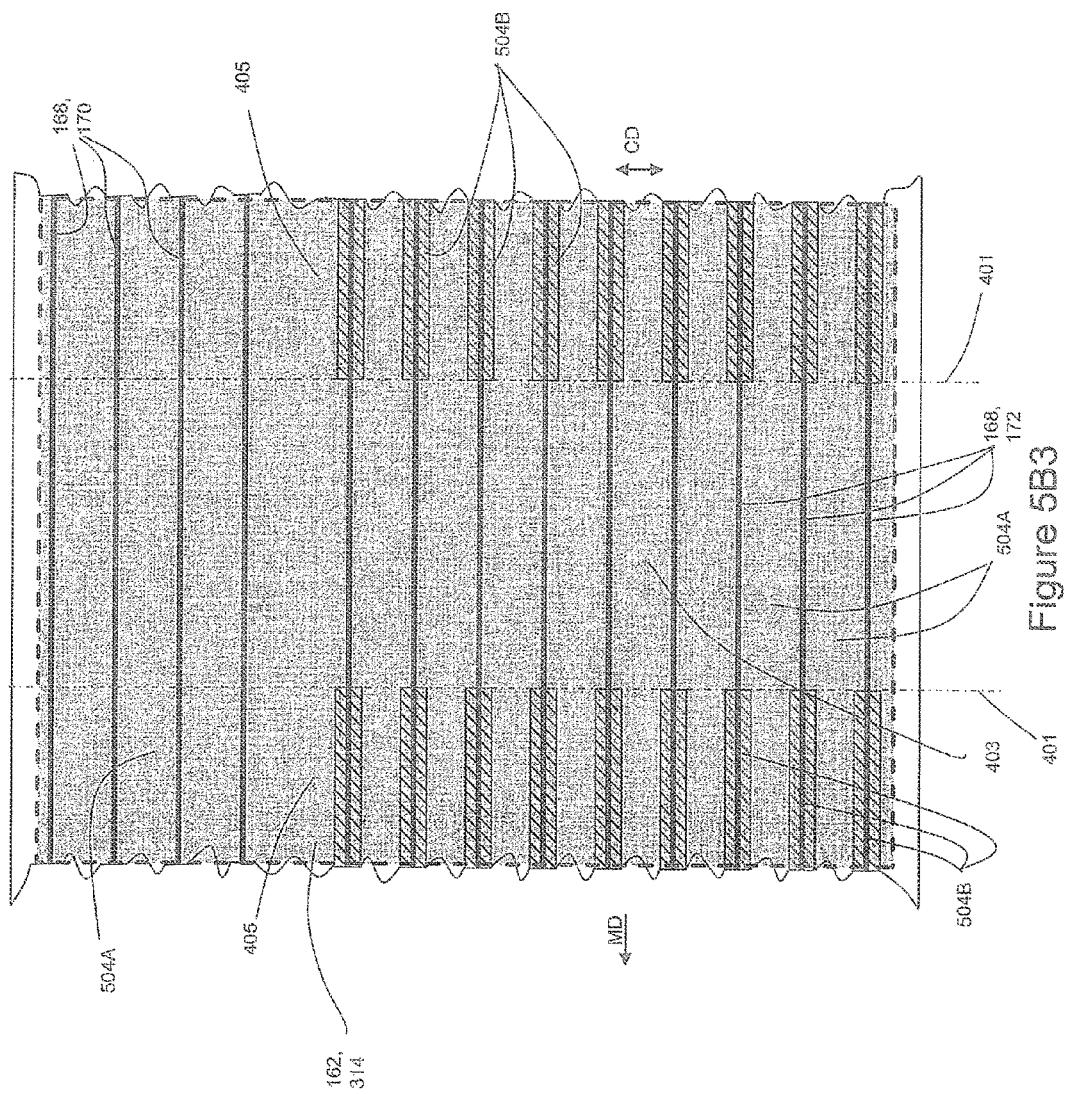

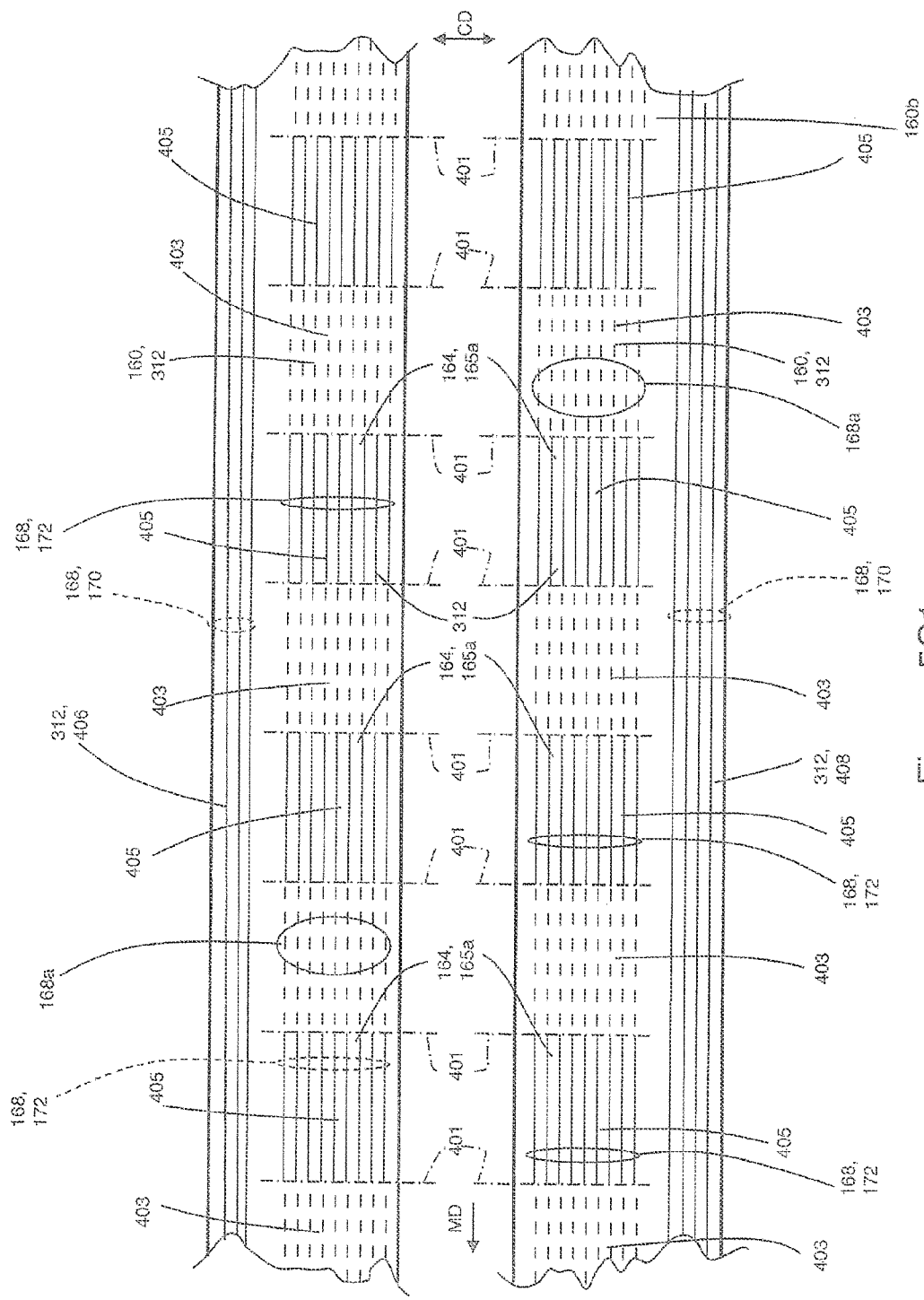
Figure 5C1

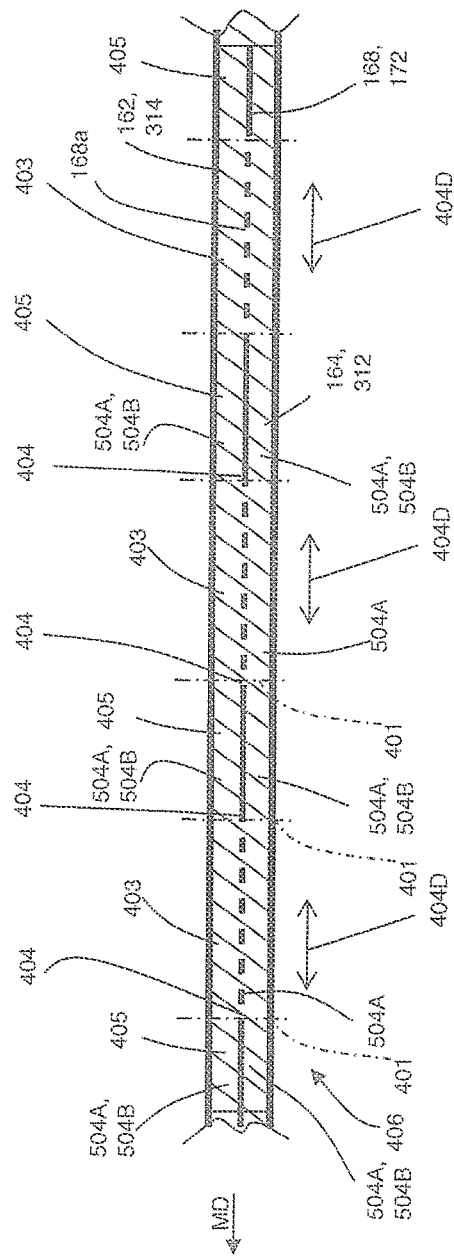
Figure 5C2
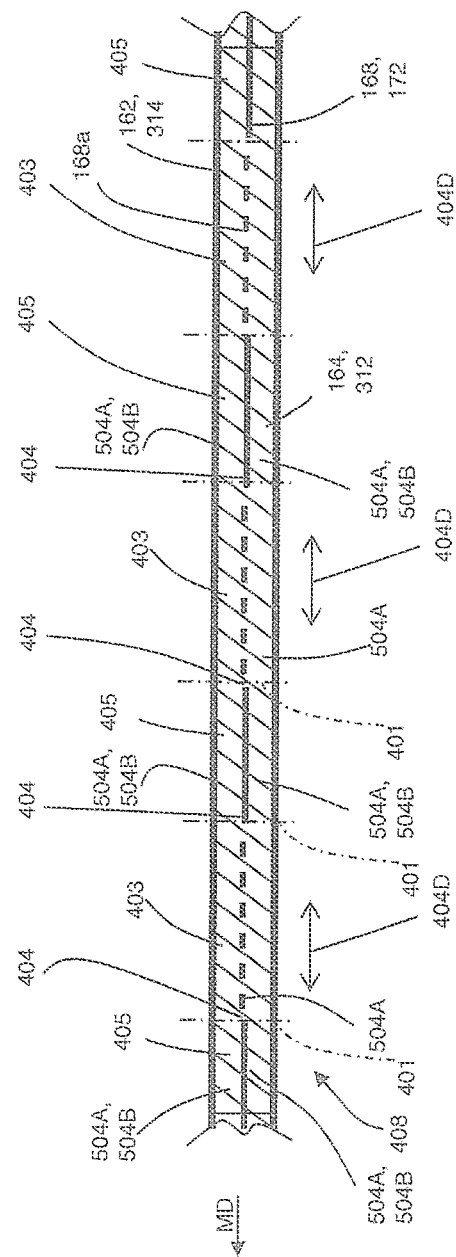
Figure 5C3

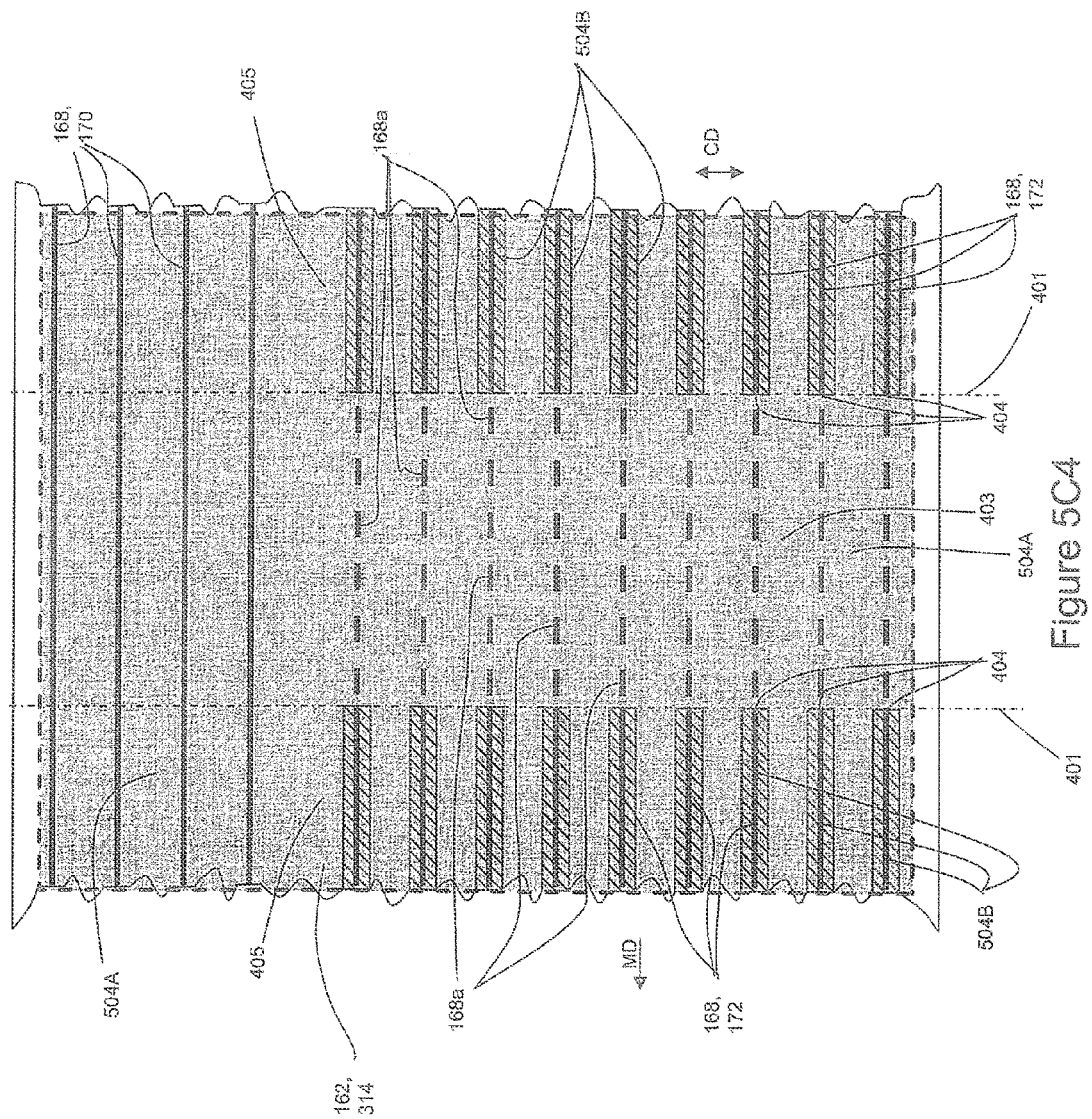
Figure 5C4

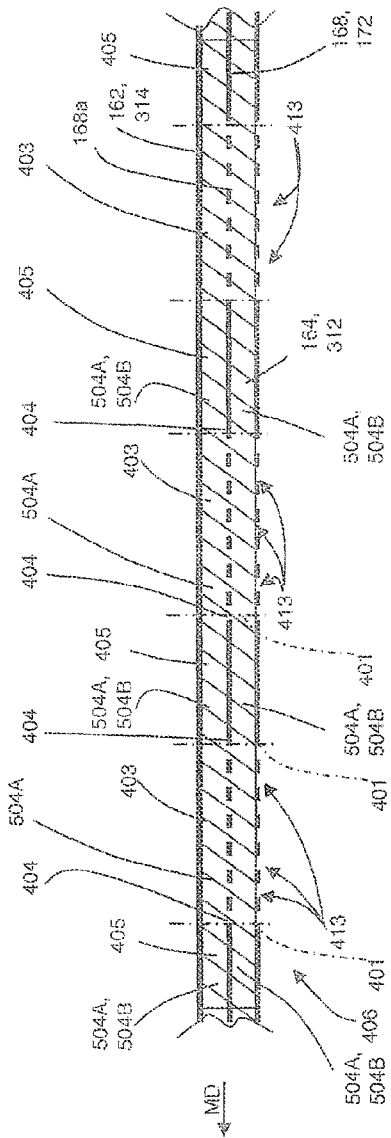
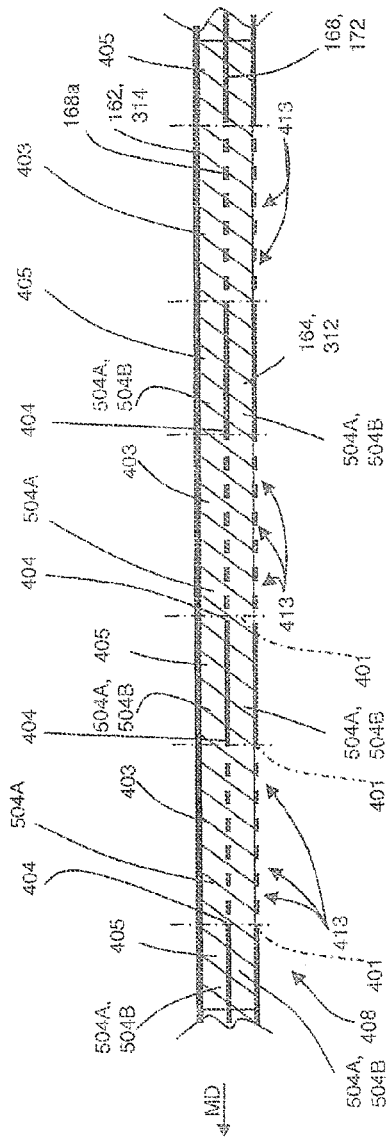
Figure 5C2A
Figure 5C3A

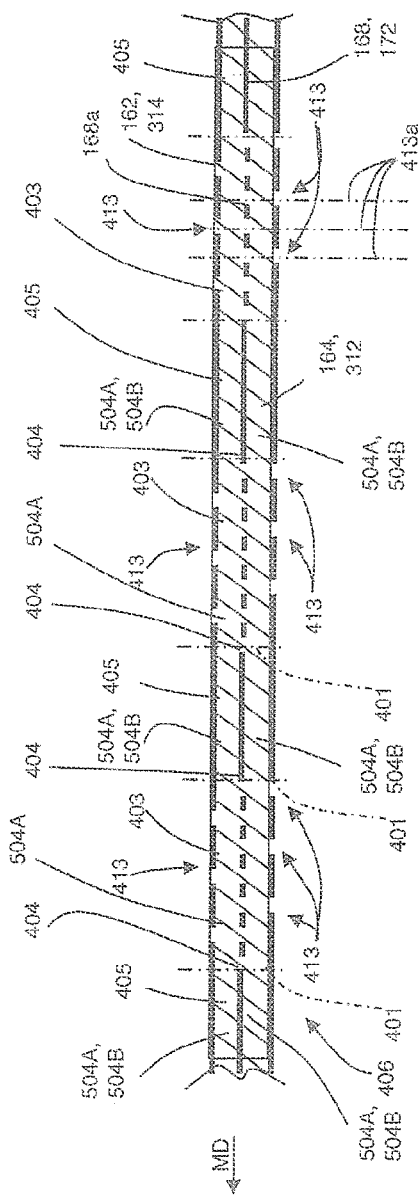
Figure 5C2B
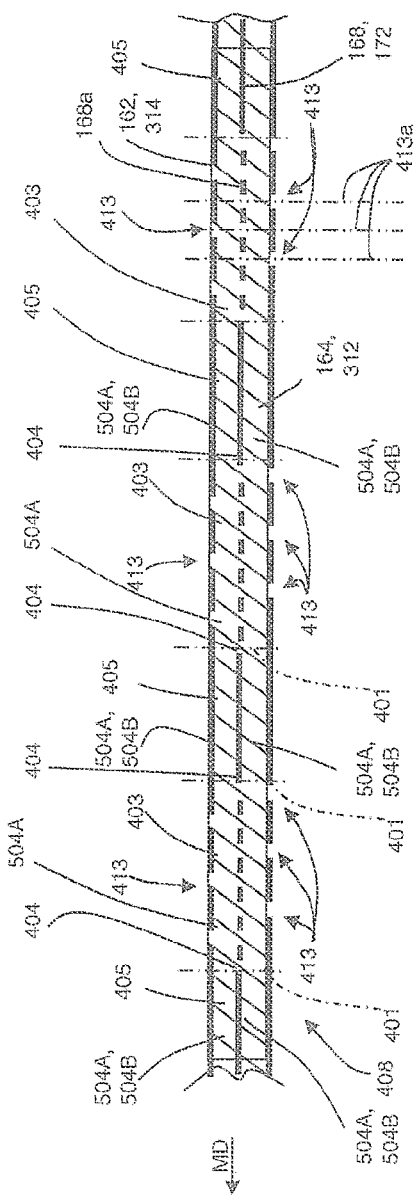
Figure 5C3B

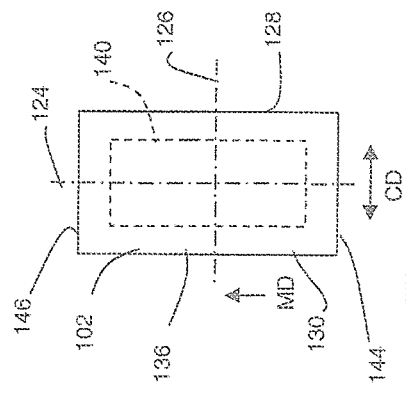
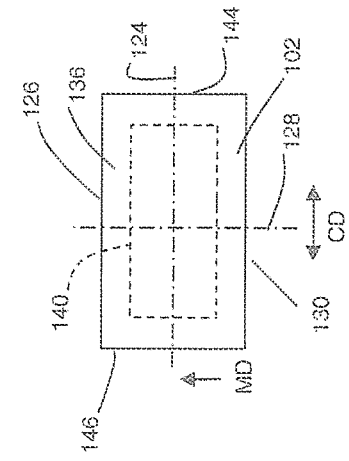
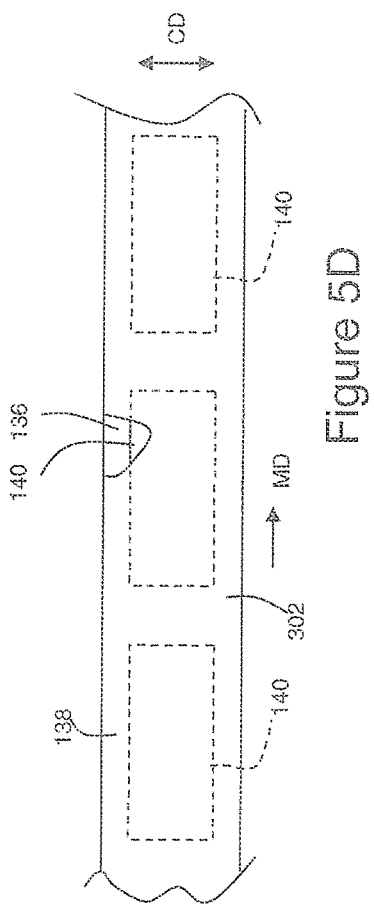
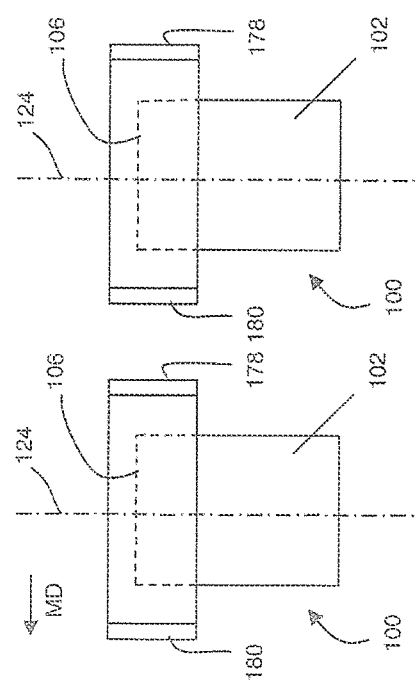

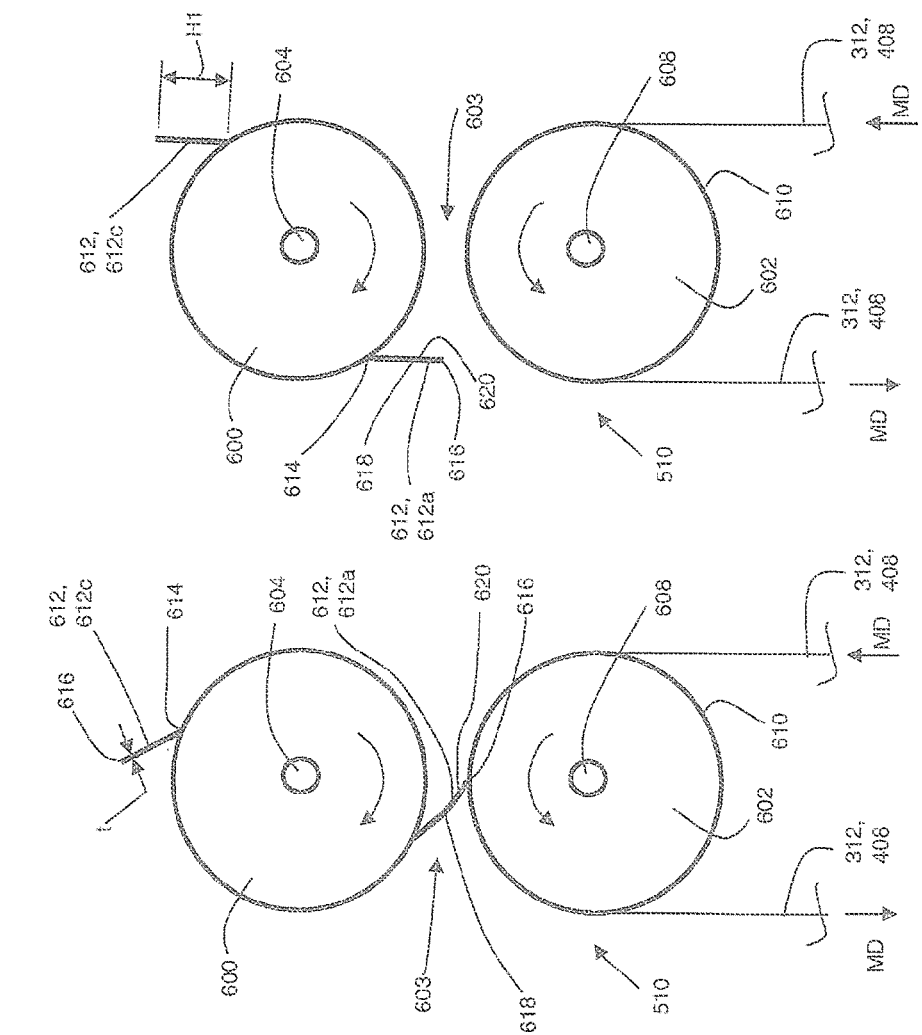

APPARATUSES AND METHODS FOR MAKING ABSORBENT ARTICLES

FIELD OF THE INVENTION

The present disclosure relates to methods for manufacturing absorbent articles, and more particularly, to apparatuses and methods for making elastic belts for diapers.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

Some diaper pant embodiments are configured with a chassis connected with front and back elastic belts, wherein opposing end regions of the front and back belts are connected with each other at side seams. In some instances, the elasticity of the front and back belts is removed in regions where the chassis connects with the belts. In some configurations, diapers may include graphics on the belts or in belt regions, and the absence of elasticity in such regions may allow for reduced distortion of graphics located in those regions. Thus, in some converting configurations adapted to assemble such diaper pants, stretched elastic strands are glued between two continuous nonwoven webs to form an elastic laminate. Regions of the elastic strands may then be intermittently deactivated along the length of the elastic laminate by cutting the elastic strands. Subsequent to deactivating the elastic strands, the elastic laminate may be subjected to additional handling and converting operations.

However, cutting the elastic strands may also damage other materials of the elastic laminate, for example the nonwoven webs, resulting in a relatively poor aesthetic appearance. In addition, the ends of the cut elastic stands may snap back in an uncontrolled fashion and consequently may end up in an undesired location within the laminate and may form a wad of elastic which may negatively impact comfort, quality impression and aesthetics. Further, deactivating the elastics in an elastic laminate may weaken the laminate, making the laminate relatively more likely to tear, and/or may otherwise result in control and handling difficulties associated with differential stretch characteristics within the laminate during subsequent processing. Consequently, it would be beneficial to provide methods and apparatuses that are configured to minimize handling of the elastic laminates after intermittently deactivating the elastics therein; and/or assemble the elastic laminate in such a way to maximize the aesthetic appearance of the laminate when placed in an assembled product.

SUMMARY OF THE INVENTION

The present disclosure relates to methods and apparatuses for assembling diapers, each including a chassis connected with front and back elastic belts. As discussed in more detail below, opposing end regions of the chassis are connected with regions of the elastic belts where the elasticity of the elastic belts has been removed or deactivated. An elastic laminate may be formed by continuously bonding elastic strands between a first continuous substrate layer and a second continuous substrate layer such that the elastic strands are bonded to both the first substrate layer and the second substrate layer in heavy-bond regions. And the elastic strands are bonded to the first substrate layer and/or the second substrate layer within light-bond regions. The elastic strands are then intermittently deactivated by cutting the strands into one or more discrete pieces in the light-bond regions. The discrete pieces retract and remain in the light-bond regions.

In one form, a method may be adapted to assemble disposable diapers, each diaper comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet. The method includes the steps of: advancing a first continuous substrate layer having a first surface and an opposing second surface in a machine direction, and defining a width in a cross direction; advancing a second continuous substrate layer having a first surface and an opposing second surface in a machine direction, and defining a width in a cross direction; applying a first adhesive continuously along the machine direction to the first surface of the first continuous substrate layer; advancing elastic strands in the machine direction in a stretched state; applying a second adhesive intermittently along the machine direction to at least one of the elastic strands, the first surface of the first continuous substrate layer, and the first surface of the second continuous substrate layer; placing the elastic strands in the stretched state between the first surface of the first substrate layer and the first surface of the second substrate layer to form an elastic laminate, the elastic laminate including first regions that include the first adhesive and not the second adhesive, and second regions including both the first adhesive and the second adhesive, the second regions intermittently spaced along the machine direction; cutting the elastic laminate along the machine direction to form a first continuous elastic laminate and a second continuous elastic laminate, each of the first continuous elastic laminate and the second continuous elastic laminate including first regions and second regions; separating the first continuous elastic laminate and the second elastic laminate in the cross direction; severing elastic strands into one or more discrete lengths in the first regions of the first continuous elastic laminate and the second elastic laminate, wherein ends of the severed elastic strands retract from the first regions to the second regions; and bonding the first end regions of each chassis with first regions of first continuous elastic laminate, and bonding the second end regions of each chassis with first regions of the second continuous elastic laminate.

In another form, a method may be configured for assembling disposable diapers, each diaper comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet. The method includes the steps of: advancing a first continuous substrate layer having a first surface and an opposing second surface in a machine direction, and defining a width in a cross direction; advancing a second continuous substrate layer having a first surface and an opposing second surface in a machine direction, and defining a width in a cross direction; applying a first adhesive continuously along the machine direction to the first surface of the first continuous substrate layer; advancing elastic strands in the machine direction in a stretched state; applying a second adhesive intermittently along the machine direction to at least one of the elastic strands, the first surface of the first continuous substrate layer, and the first surface of the second continuous substrate layer; placing the elastic strands in the stretched state between the first surface of the first substrate layer and the first surface of the second substrate layer to form an elastic laminate, the elastic laminate including first regions that include the first adhesive and not the second adhesive, and second regions including both the first adhesive and the second adhesive, the second regions intermittently spaced along the machine direction; and severing elastic strands into one or more discrete lengths in the first regions of the elastic laminate, wherein the ends of the severed elastic strands retract from the first regions to the second regions.

BRIEF DESCRIPTION OF THE DRAWINGS

FIG. 2A is a partially cut away plan view of the diaper pant shown in FIG. 1.

FIG. 2B is a partially cut away plan view of a second embodiment of a diaper pant.

FIG. 3A is a cross-sectional view of the diaper pants of FIGS. 2A and 2B taken along line 3A-3A.

FIG. 3B is a cross-sectional view of the diaper pants of FIGS. 2A and 2B taken along line 3B-3B.

FIG. 4A shows a first alternative converting embodiment for forming an elastic laminate.

FIG. 4A1 is a view of a continuous length of an elastic laminate from FIG. 4A taken along line 4A1-4A1.

FIG. 4B shows a second alternative converting embodiment for forming an elastic laminate.

FIG. 4B1 is a view of a continuous length of an elastic laminate from FIG. 4B taken along line 4B1-4B1.

FIG. 4B2 is a view of a continuous length of an elastic laminate from FIG. 4B taken along line 4B2-4B2.

FIG. 5B1 is a cross-sectional view of the first belt substrate from FIG. 5B taken along line B1-B1.

FIG. 5B2 is a cross-sectional view of the second belt substrate from FIG. 5B taken along line B2-B2.

FIG. 5B3 shows a detailed view of a belt substrate with the outer layer belt material cut-away to illustrate an adhesive application embodiment.

FIG. 5C1 is a view of the first and second belt substrates material from FIG. 5C with the outer layer belt material cut-away to illustrate the deactivated elastics in the light-bond regions.

FIG. 5C2 is a cross-sectional view of the first belt substrate from FIG. 5C taken along line C2-C2 showing deactivated elastics in the light-bond regions.

FIG. 5C3 is a cross-sectional view of the second belt substrate from FIG. 5C taken along line C3-C3 showing deactivated elastics in the light-bond regions.

FIG. 5C4 shows a detailed view of a belt substrate from FIG. 5C with the outer layer belt material cut-away to illustrate the deactivated elastics in the light-bond regions.

FIG. 5C2A is a cross-sectional view of the first belt substrate from FIG. 5C taken along line C2-C2 showing elastics and inner belt material cut in light-bond regions.

FIG. 5C3A is a cross-sectional view of the second belt substrate from FIG. 5C taken along line C3-C3 showing elastics and inner belt material cut in light-bond regions.

FIG. 5C2B is a cross-sectional view of the first belt substrate from FIG. 5C taken along line C2-C2 showing elastics, inner belt material, and outer belt material cut in light-bond regions.

FIG. 5C3B is a cross-sectional view of the second belt substrate from FIG. 5C taken along line C3-C3 showing elastics, inner belt material, and outer belt material cut in light-bond regions.

FIG. 5D is a view of a continuous length of chassis assemblies from FIG. 4 taken along line D-D.

FIG. 5E1 is a view of a discrete chassis from FIG. 4 taken along line 5E1-5E1.

FIG. 5E2 is a view of a discrete chassis from FIG. 4 taken along line 5E2-5E2.

FIG. 5H is a view of two discrete absorbent articles advancing the machine direction MD from FIG. 4 taken along line 5H-5H.

FIG. 8A is a left side view of the cutting apparatus of FIG. 7 showing the blade initiating contact with the substrate partially wrapped around the anvil roll.

FIG. 8B shows the cutting apparatus of FIG. 8A as the blade flexes while being rotated into contact with the substrate partially wrapped around the anvil roll.

FIG. 8C shows the cutting apparatus of FIG. 8B after the blade is rotated away from the substrate partially wrapped around the anvil roll.

DETAILED DESCRIPTION OF THE INVENTION

Figure 1:
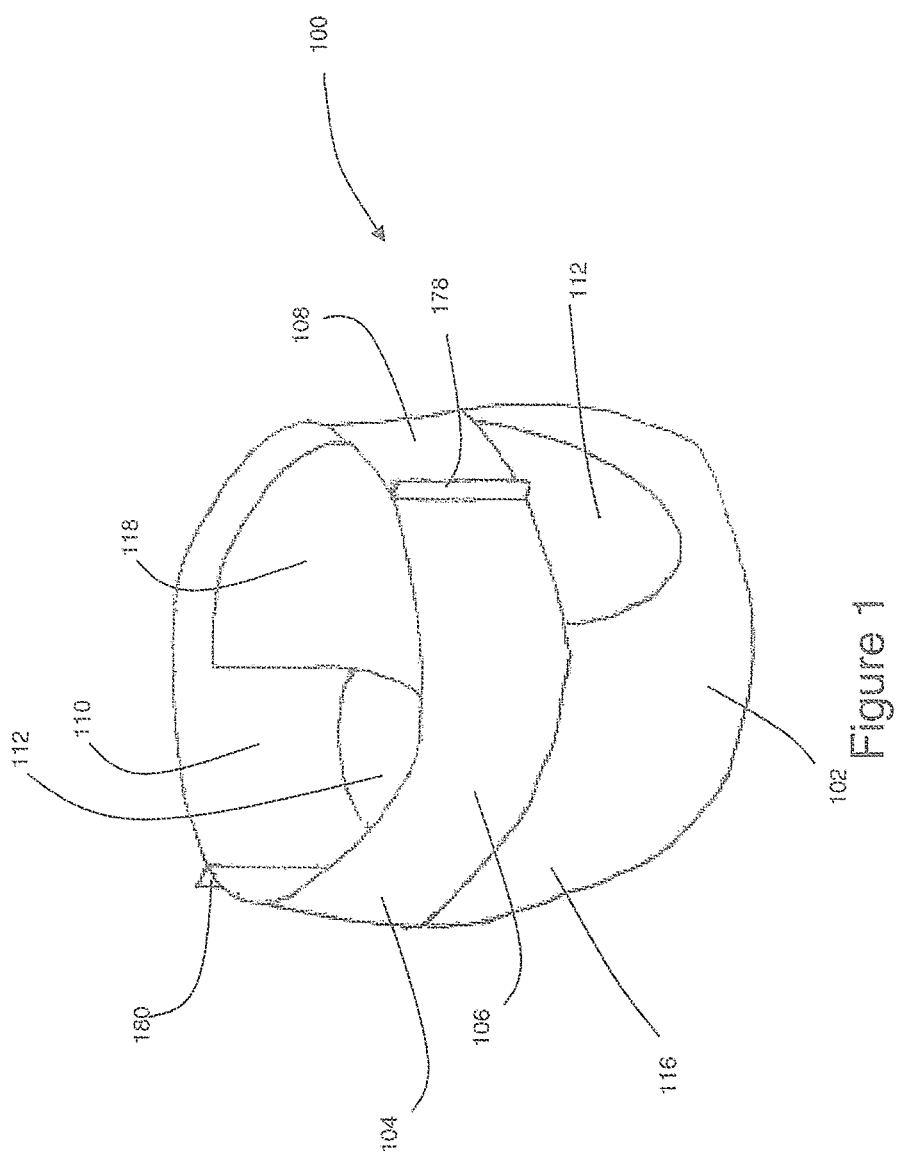
FIG. 1 is a perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a defined woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "preclosed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed.

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. As discussed in more detail below, a diaper pant can be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers can be preformed anywhere along the circumference of the waist region (e.g., side fastened or connected, front waist fastened or connected, rear waist fastened or connected).

The present disclosure relates to methods and apparatuses for assembling absorbent articles, and more particularly, diapers, each including a chassis connected with front and back elastic belts. The chassis may include a topsheet, a backsheet, and an absorbent core disposed between the topsheet and the backsheet. The chassis may also have a first end region and an opposing second end region separated from each other by a central region. As discussed in more detail below, opposing end regions of the chassis are connected with regions of the elastic belts where the elasticity of the elastic belts has been removed or deactivated. An elastic laminate may be formed by continuously bonding elastic strands between a first continuous substrate layer and a second continuous substrate layer such that a first adhesive (referred to herein as the "substrate adhesive") is continuously applied at a relatively low basis weight to the first and/or second continuous substrate layers. A second adhesive (referred to herein as the "elastic adhesive") is also intermittently applied to the elastic strands. As such, the elastic laminate includes first regions (referred to herein as "heavy-bond" regions) and second regions (referred to herein as "light-bond" regions) intermittently spaced along the machine direction, wherein the elastic strands are bonded to both the first substrate layer and the second substrate layer in the heavy-bond regions with both the substrate adhesive and the elastic adhesive. And the elastic strands are bonded to the first substrate layer and/or the second substrate layer with the substrate adhesive in the light-bond regions. The elastic laminate is then cut along the machine direction to form a first continuous elastic laminate and a second continuous elastic laminate, each of the first continuous elastic laminate and the second continuous elastic laminate including heavy-bond regions and light-bond regions. The first continuous elastic laminate and the second elastic laminate are then separated from each other in the cross direction. The elastic strands are then intermittently deactivated by cutting the strands into one or more discrete pieces in the light-bond regions of the first continuous elastic laminate and the second elastic laminate.

The discrete pieces of the elastic strands retract and remain in the light-bond regions. Although the discrete pieces of elastic strands are bonded to the first and second substrates by the substrate adhesive in the light bond regions, the substrate adhesive is not strong enough to hold the severed elastic ends of the discrete pieces elastic strands in position on the first and second substrates in the light bond regions. As such, the discrete pieces of elastic strands retract to an unstretched state in the light-bond regions. The adhesive in the light-bond regions may, however, be strong enough to help control the rate at which the discrete pieces retract. Thus, the severed elastic pieces may be configured to retract in the light-bond regions at a controlled rate dictated in part by the basis weight, adhesive application type, and/or type of substrate adhesive applied in the light-bond regions. A relatively slow rate of retraction or snap back of severed the elastic pieces may result in improved consistency and/or predictability of the location of the elastic pieces within the completed elastic laminate. As such, the first continuous elastic laminate and the second continuous elastic laminate each have elastic regions corresponding with the first regions, and deactivated regions corresponding with the second regions where the elastics have been cut into pieces. A plurality of chassis may then be bonded between first and second elastic laminates, wherein first and second end regions of each chassis is bonded with light-bond regions of first and second continuous elastic laminates.

It is to be appreciated that the elastic laminate can be formed in various ways. For example, in some embodiments, the first continuous substrate layer may be formed from a first continuous substrate, and the second continuous substrate layer may be formed from a second continuous substrate. In other embodiments, the first continuous substrate layer and/or the second continuous substrate layer may be formed by folding a portion of a single continuous substrate onto another portion of the single continuous substrate.

Having the substrate adhesives in the light-bond regions may help enable the elastic to be cut more uniformly as the adhesive holds the elastic in position long enough for a plurality of cuts to be performed. In addition, the adhesive may allow the elastic to retract while at the same time providing enough adhesion to prevent the elastic from becoming dislodged from the assembled absorbent article, which may lead to poor quality impressions with consumers.

The processes and apparatuses discussed herein may be used to assemble elastic laminates in various types of substrate configurations, some of which may be used in the manufacture of different types of absorbent articles. To help provide additional context to the subsequent discussion of the process embodiments, the following provides a general description of absorbent articles in the form of diapers that include elastic laminates that may be assembled in accordance with the methods and apparatuses disclosed herein. Although the methods and apparatuses herein are discussed below in the context of manufacturing absorbent articles, it is to be appreciated that the assembly methods and apparatuses herein may be configured to manufacture various types of substrates having intermittently spaced elastic and inelastic regions.

FIGS. 1 and 2A show an example of a diaper pant 100 that may be assembled and folded in accordance with the apparatuses and methods disclosed herein. In particular, FIG. 1 shows a perspective view of a diaper pant 100 in a pre-fastened configuration, and FIG. 2A shows a plan view of the diaper pant 100 with the portion of the diaper that faces away from a wearer oriented towards the viewer. The diaper pant 100 shown in FIGS. 1 and 2A includes a chassis 102 and a ring-like elastic belt 104. As discussed below in more detail, a first elastic belt 106 and a second elastic belt 108 are connected together to form the ring-like elastic belt 104.

With continued reference to FIG. 2A, the chassis 102 includes a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 120 in the front waist region 116 and a longitudinally opposing and laterally extending back waist edge 122 in the back waist region 118. To provide a frame of reference for the present discussion, the diaper 100 and chassis 102 of FIG. 2A is shown with a longitudinal axis 124 and a lateral axis 126. In some embodiments, the longitudinal axis 124 may extend through the front waist edge 120 and through the back waist edge 122. And the lateral axis 126 may extend through a first longitudinal or right side edge 128 and through a midpoint of a second longitudinal or left side edge 130 of the chassis 102.

As shown in FIGS. 1 and 2A, the diaper pant 100 may include an inner, body facing surface 132, and an outer, garment facing surface 134. The chassis 102 may include a backsheet 136 and a topsheet 138. The chassis 102 may also include an absorbent assembly 140 including an absorbent core 142 that may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 120 in the front waist region 116 and the laterally extending back waist edge 122 in the back waist region 118. When the diaper pant 100 is worn on the lower torso of a wearer, the front waist edge 120 and the back waist edge 122 of the diaper pant 100 may encircle a portion of the waist of the wearer. At the same time, the chassis side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, to allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; and 4,704,115; and U.S. Patent Publication No. 2009/0312730A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1.

As previously mentioned, the ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2A, 3A, and 3B, the first elastic belt 106 also defines an outer lateral edge 107a and an inner lateral edge 107b, and the second elastic belt 108 defines an outer lateral edge 109a and an inner lateral edge 109b. The outer longitudinally opposed edges 107a, 109a may also define the front waist edge 120 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172.

As shown in FIG. 2A, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2A, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend continuously across the entirety of the central regions 106c, 108c of the first and second elastic belts 106, 108. As discussed in more detail below and as shown in FIGS. 2A and 2B, the inner, waist elastics 172 may be cut into one or more discrete lengths or pieces 168a in the central regions 106c, 108c of the first and second elastic belts 106, 108. More particularly, the elastic strands 172 are cut into pieces 168a and are deactivated in the central regions 106c, 108c. As such, elasticity imparted by the elastic strands 172 is removed from the first and second elastic belts 106, 108 in the regions where the elastic strands 172 are cut into pieces 168a.

Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. It is also to be appreciated that the elastic strands may have a variable decitex and/or opacity. Further, in some embodiments, elastic strands may extend along straight lines and/or curved lines. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt.

It is to be appreciated that the chassis 102 and elastic belts 106, 108 may be configured in different ways other than as depicted in FIG. 2A. For example, FIG. 2B shows a plan view of a diaper pant 100 having the same components as described above with reference to FIG. 2A, except the first laterally extending end edge 144 of the chassis 102 is aligned along and coincides with the outer lateral edge 107a of the first elastic belt 106, and the second laterally extending end edge 146 is aligned along and coincides with the outer lateral edge 109a of the second belt 108.

Figure 4:
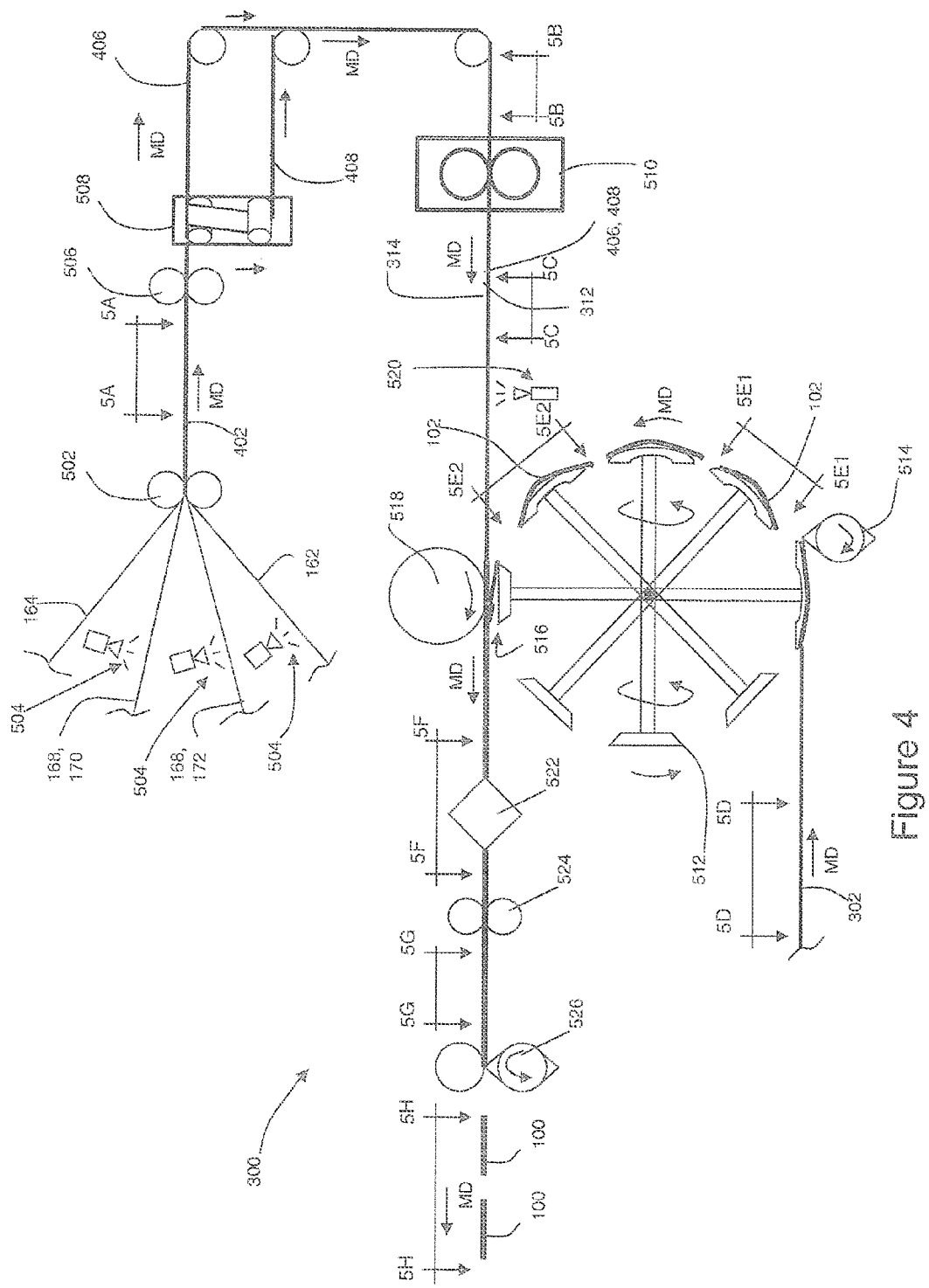
FIG. 4 is a schematic side view of a converting apparatus adapted to manufacture pre-fastened, pant diapers.

As previously mentioned, the apparatuses and methods according to the present disclosure may be utilized to assemble various components of diapers 100. For example, FIG. 4 shows a schematic view of a converting apparatus 300 adapted to manufacture pant diapers 100. The method of operation of the converting apparatus 300 may described with reference to the various components of pant diapers 100 described above and shown in FIGS. 1 and 2A. Although the following methods are provided in the context of the diaper 100 shown in FIGS. 1 and 2A, it is to be appreciated that various embodiments of diapers and associated components, such as for example leg cuffs and waist bands, can be manufactured according the methods disclosed herein, such as for example, the absorbent articles disclosed in U.S. Pat. Nos. 7,569,039 and 5,745,922; U.S. Patent Publication Nos. 2005/0107764A1, 2012/0061016A1, and 2012/0061015A1; and the U.S. patent application entitled "Methods and Apparatuses for Making Leg Cuffs for Absorbent Articles," filed Mar. 30, 2012, which are all hereby incorporated by reference herein.

As described in more detail below, the converting apparatus 300 shown in FIG. 4 operates to advance discrete chassis 102 along a machine direction MD initially with the longitudinal axis parallel to the machine direction and subsequently cutting the chassis web and turning the separate chassis such that the lateral axis of each chassis 102 is parallel with the machine direction, and wherein the chassis 102 are spaced apart from each other along the machine direction. Opposing waist regions 116, 118 of the spaced apart chassis 102 are then connected with continuous lengths of advancing first and second elastic belt substrates 406, 408. The chassis 102 are then folded along the lateral axis to bring the first and second elastic belt substrates 406, 408 into a facing relationship, and the first and second elastic belt substrates are connected together along intermittently spaced seams 336. And the elastic belt substrates 406, 408 are cut along the seams 336 to create discrete diapers 100, such as shown in FIG. 1.

Figure 5A:
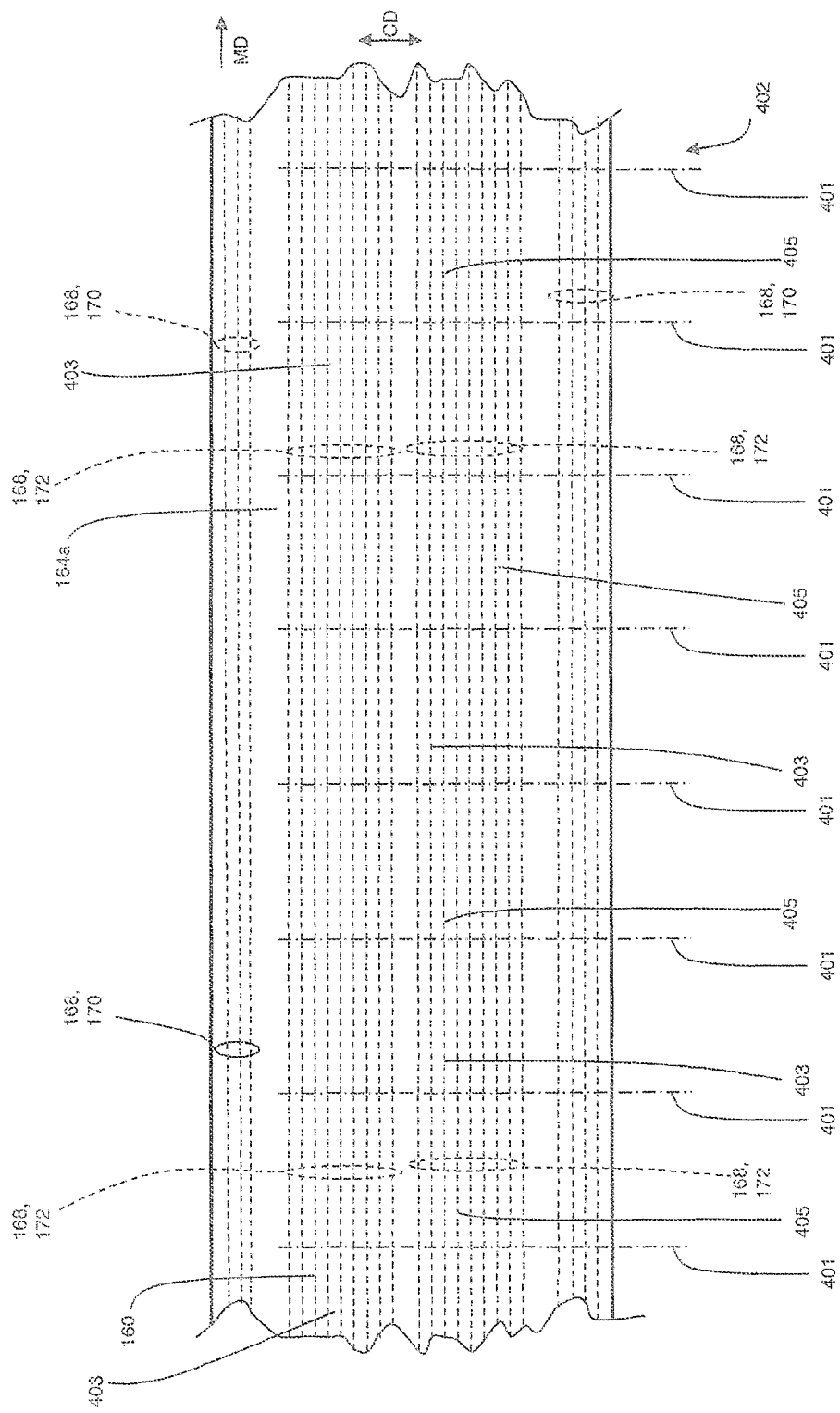
FIG. 5A is a view of a continuous length of an elastic laminate from FIG. 4 taken along line 5A-5A.

As shown in FIGS. 4 and 5A, a first continuous substrate layer in the form of a continuous length of outer layer belt material 162; a second continuous substrate layer in the form of a continuous length of inner layer belt material 164; and elastics 168 are combined to form a continuous elastic laminate in the form of a belt material 402. More particularly, continuous lengths of outer layer belt material 162, inner layer belt material 164, outer elastic strands 170 and inner elastic strands 172 are advanced in a machine direction MD and combined at nip rolls 502 to form a continuous length of belt material 402. Before entering the nip rolls 502, the outer elastic strands 170 and inner elastic strands 172 are stretched in the machine direction MD. In addition, adhesive 504 may be applied to the elastic strands 170, 172 as well as either or both of the continuous lengths of outer layer belt material 162 and inner layer belt material 164 before entering nip rolls 502. More particularly, a first adhesive 504A (referred to herein as "substrate adhesive") may be continuously applied to the either or both of the continuous lengths of outer layer belt material 162 and inner layer belt material 164. Further, a second adhesive 504B (referred to herein as "elastic adhesive") may be applied intermittently along the lengths of the inner elastic strands 172 and/or intermittently along the length of either or both of the continuous lengths of outer layer belt material 162 and inner layer belt material 164 before entering nip rolls 502. For the purposes of clarity, the substrate adhesive 504A is represented by shaded or darkened regions in FIGS. 5B3 and 5C4; and the elastic adhesive 504B is represented by cross-hatch regions surrounding portions of elastics 168, 172 in FIGS. 5B3 and 5C4.

As such, the substrate adhesive 504A may be applied to one or more of the outer layer belt material 162, the inner layer belt material 164, the outer elastic strands 170, and the inner elastic strands continuously along the machine direction MD. In addition, the elastic adhesive 504B is intermittently applied to the inner elastic strands 172 and/or either or both of the continuous lengths of outer layer belt material 162 and inner layer belt material 164 along the machine direction MD. More particularly, as shown in FIG. 5A, the belt material 402 may include first regions 403 (referred to herein as "light-bond regions") intermittently spaced between second regions 405 (referred to herein as "heavy-bond regions") 405 along the machine direction MD. Thus, the inner elastic strands 172 are bonded to either the outer layer belt material 162 or inner layer belt material 164 in the light-bond regions 403 with only the substrate adhesive 504A. And the inner elastic strands 172 are bonded to the outer layer belt material 162 and/or inner layer belt material 164 in the heavy-bond regions 405 with elastic adhesive 504B and in certain embodiments the substrate adhesive 504A or combinations thereof. For the purposes of clarity, dashed lines 401 are shown in FIG. 5A and others to represent example boundaries between the light-bond regions 403 and the heavy-bond regions 405. It is to be appreciated that such boundaries between the light-bond regions 403 and the heavy-bond regions 405 can also be curved, angled, and/or straight. It is to be appreciated that in some embodiments, the heavy-bond regions may continuously extend from one side edge of a substrate layer to a laterally opposing side edge, while the light-bond regions may be laterally discontinuous. It is also to be appreciated that the elastic adhesive 504B and/or the substrate adhesive 504A can be intermittently applied and alternating along the machine direction such that the elastics are continuously bonded, but with alternating adhesive applications. It is also to be appreciated that in some embodiments, the elastic adhesive 504B and/or the substrate adhesive 504A can be intermittently applied such that the application of the adhesives overlap with each other.

Although FIG. 4 shows an embodiment wherein the belt material 402 is formed by combining continuous lengths of outer layer belt material 162 and inner layer belt material 164 with elastic strands 168, it is to be appreciated the belt material 402 can be formed in various other ways. As previously mentioned, the first continuous substrate layer and the second continuous substrate layer may be formed by a folding portion of a single continuous substrate onto another portion of the single continuous substrate. For example, FIG. 4A shows an embodiment wherein the belt material 402 is formed by combining continuous lengths of elastic strands 168 with a single continuous length of belt material 160 having a first surface 161a and an opposing second surface 161b. More particularly, the continuous lengths of outer elastic strands 170 and inner elastic strands 172 are advanced in a machine direction MD and combined with the first surface 161a of the belt material 160 at drum 528. Before being combined at drum 528, the outer elastic strands 170 and inner elastic strands 172 are stretched in the machine direction MD. From the drum 528, the combined elastics 170, 172 and the belt material 160 advance to a folding apparatus 530 adapted to fold a portion of the first surface 161a of the belt material 160 onto another portion of the first surface 161a such that the elastics 170, 172 are intermittently bonded between the folded portions of the belt material 160. In the arrangement shown in FIGS. 4A and 4A1, elastic adhesive 504B may be applied intermittently to the elastic strands 170, 172 and/or the continuous length of belt material 160 before entering the folder 530. For example, FIG. 4A1 shows an arrangement wherein the belt material 160 includes opposing longitudinal edges 160a, 160b and laterally opposed edge regions 166a, 166b separated by a central region 166c. And the elastics are combined with the central region 166c of the first surface 161a of the belt material 160. The folder 530 folds the opposing edge regions 166a, 166b onto the central region 166c. As such, the elastics are sandwiched between the first surface 161a of the opposing edge regions 166a, 166b and the first surface 161a of the central region 166c. Thus, an elastic laminate can be formed wherein the first substrate layer may comprise the central region 166c, and wherein the second substrate layer may comprise the folded edge regions 166a, 166b. From the folder 530, the combined elastics 168 and the belt material 160 may enter nip rolls 502 to form the belt material 402.

It is to be appreciated that the belt material may be folded in various ways at the 530. For example, in some embodiments, the elastics 168 may be combined with the belt material 160 in such a way that the folder 530 need only fold the belt material 160 once along the center region 166c. For example, the folder 530 may fold the first surface 161a of the belt material 160 onto itself such that the first longitudinal edge 161a is aligned with the second longitudinal edge 161b.

Figure 2:
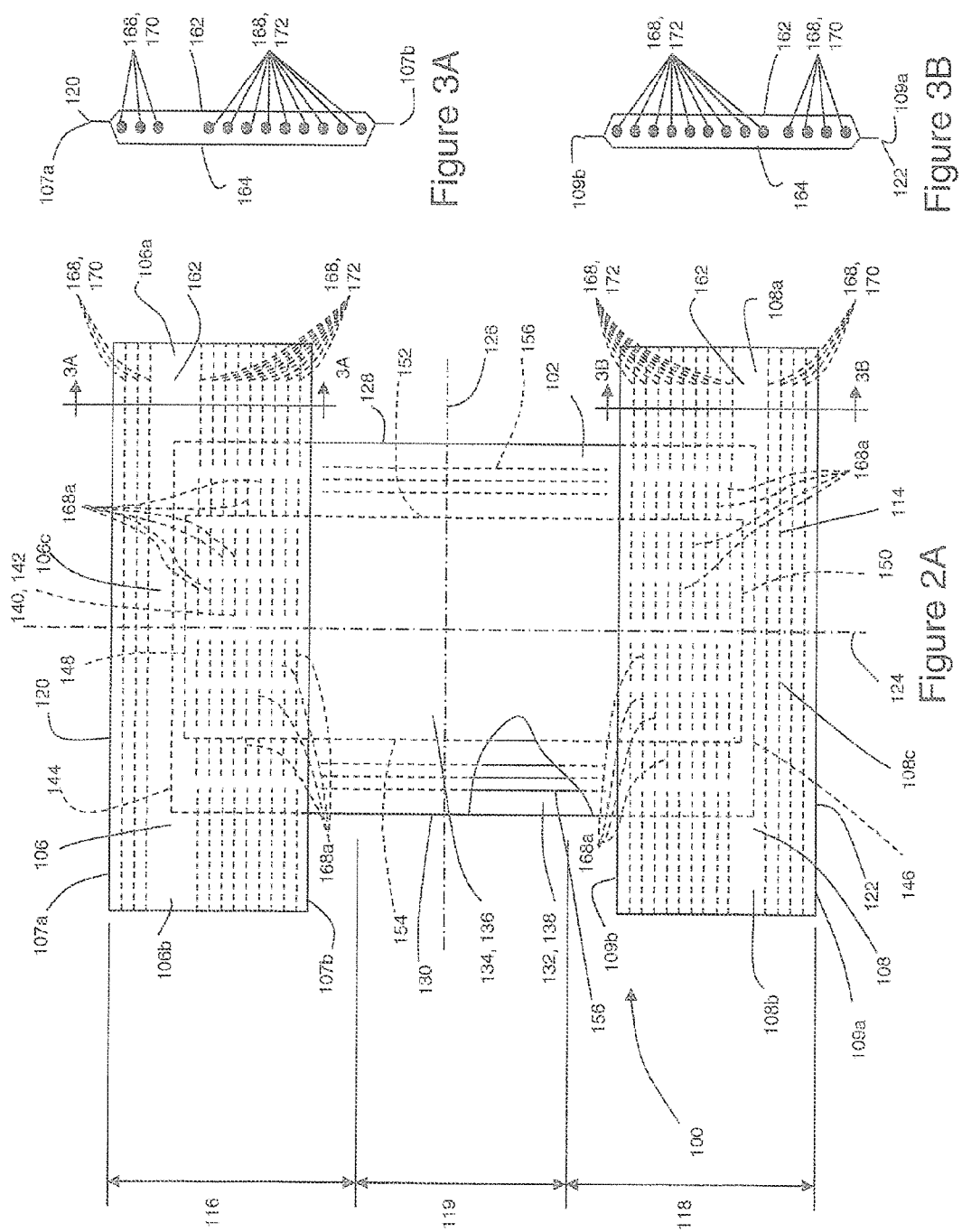

In yet another example embodiment shown in FIG. 4B, the belt material 402 is formed by first combining continuous lengths of outer elastic strands 170 with the opposing edge regions 166a, 166b of single continuous length of belt material 160 at drum 528. Before being combined at drum 528, the outer elastic strands 170 are stretched in the machine direction MD. From the drum 528, the combined elastics 170 and the belt material 160 advance to a folding apparatus 530 adapted to fold the opposing edge regions 166a, 166b onto themselves. As such, the outer elastics 170 are sandwiched between first surfaces 161a of the opposing edge regions 166a, 166b, such as shown in FIG. 4B1. From the folder 530, the outer elastics 170 and belt material 160 are combined with the inner elastics 172 and the inner belt material 164 at nip rolls 502 to form the belt material 402 as shown in FIG. 4B2. Thus, an elastic laminate can be formed wherein the first substrate layer may comprise the central region 166c, and wherein the second substrate layer may comprise the folded edge regions 166a, 166b. In the arrangement shown in FIGS. 4B-4B2, elastic adhesive 504B may be applied to the elastic strands 170 and/or the continuous length of belt material 160 before entering the folder 530.

Figure 5B:
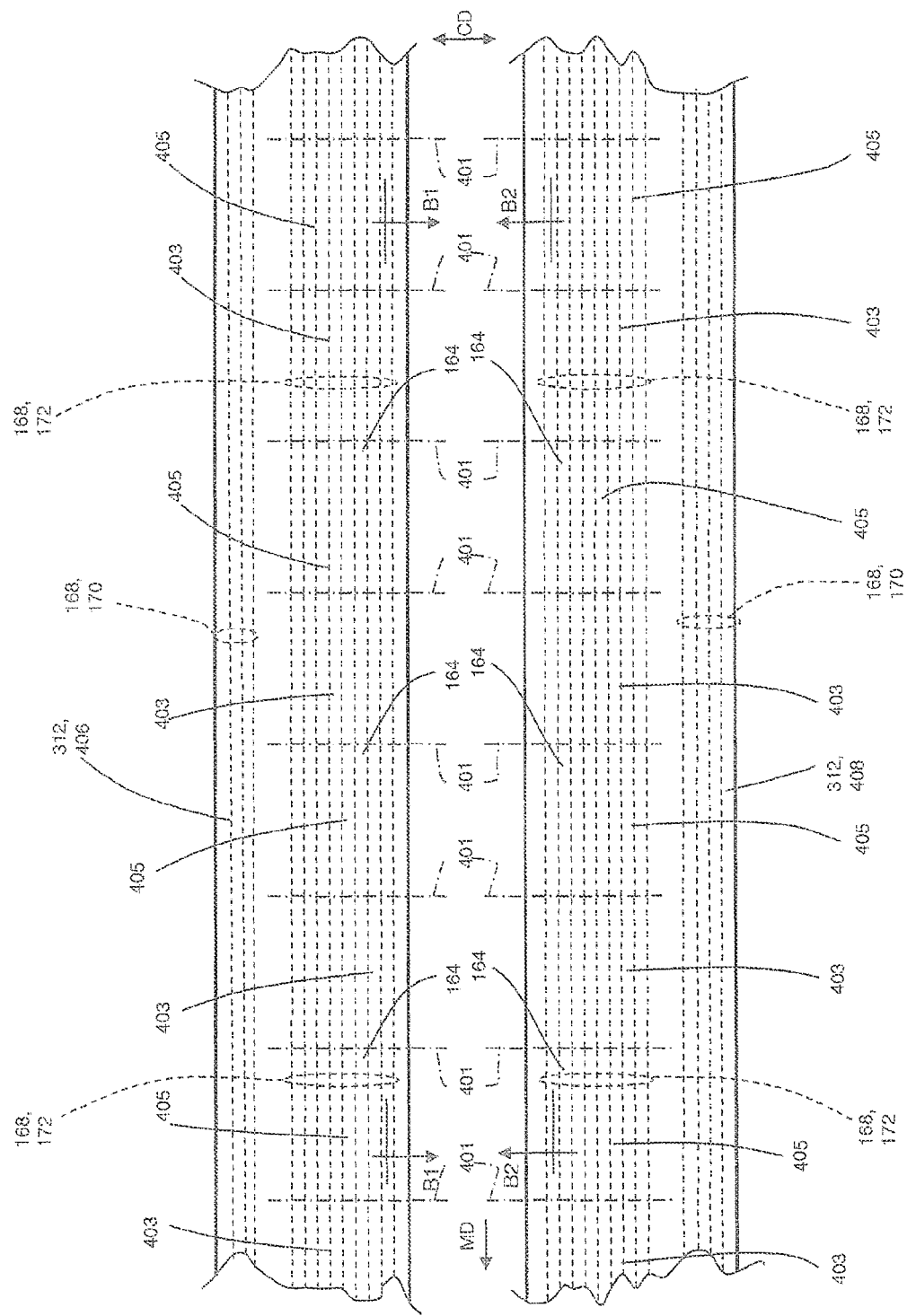
FIG. 5B is a view of the elastic laminate from FIG. 4 after being slit into first and second belt substrates separated from each other in the cross direction CD taken along line 5B-5B.

Referring back to FIG. 4, from the nip rolls 502 the continuous length of belt material 402 advances in the machine direction MD to a cutter 506 that cuts the belt material 402 into two continuous belt substrates, referred to as a first belt substrate 406 and a second belt substrate 408. The cutter 506 may be configured in various ways. For example, in some embodiments the cutter 506 may be a slitter or a die cutter that separates the belt material into two continuous belt substrates with either a straight line cut and/or a curved line cut. The cutter 506 may also be configured as a perforator that perforates the belt material with a line of weakness and wherein the belt material is separated along the line of weakness in a later step. From the cutter 506, the first and second belt substrates 406, 408 advance through a diverter 508 that separates the first and second belt substrates from each other in the cross direction CD, such as shown in FIG. 5B. The elastic strands 170, 172, and thus, the continuous length of first and second belt substrates 406, 408 are maintained in a stretched condition while advancing along the machine direction MD.

It is to be appreciated that the diverter 508 may be configured in various ways. For example, in some embodiments, the diverter 508 may include turn bars angled at 45 degrees or some other angle with respect to the machine direction. In some embodiments, the diverter may include cambered rollers. Other embodiments may include diverters in the form of a pivot table, such as, for example, the FIFE-500 Web Guiding System, by Maxcess-FIFE Corporation. The diverter may also include instrumentation and web edge control features that allow for precise active control of the substrate positions.

With continued reference to FIGS. 4, 5B, 5B1, 5B2, and 5B3, the first and second belt substrates 406, 408 advance from the diverter 508 to a cutting unit 510. The cutting unit 510 then intermittently deactivates the elastics 168 in the first and second belt substrates 406, 408. More particularly, the cutting unit 510 may sever, cut, and/or break the inner elastics 168, 172 in the light-bond regions 403 into one or more discrete pieces 168a of elastic material. As such, the first and second belt substrates 406, 408 each have elastic regions 405 corresponding with the heavy-bond regions 405, and deactivated regions 403 corresponding with the light-bond regions 403 where the elastics 172 have been cut into discrete pieces 168a.

Figure 5C:
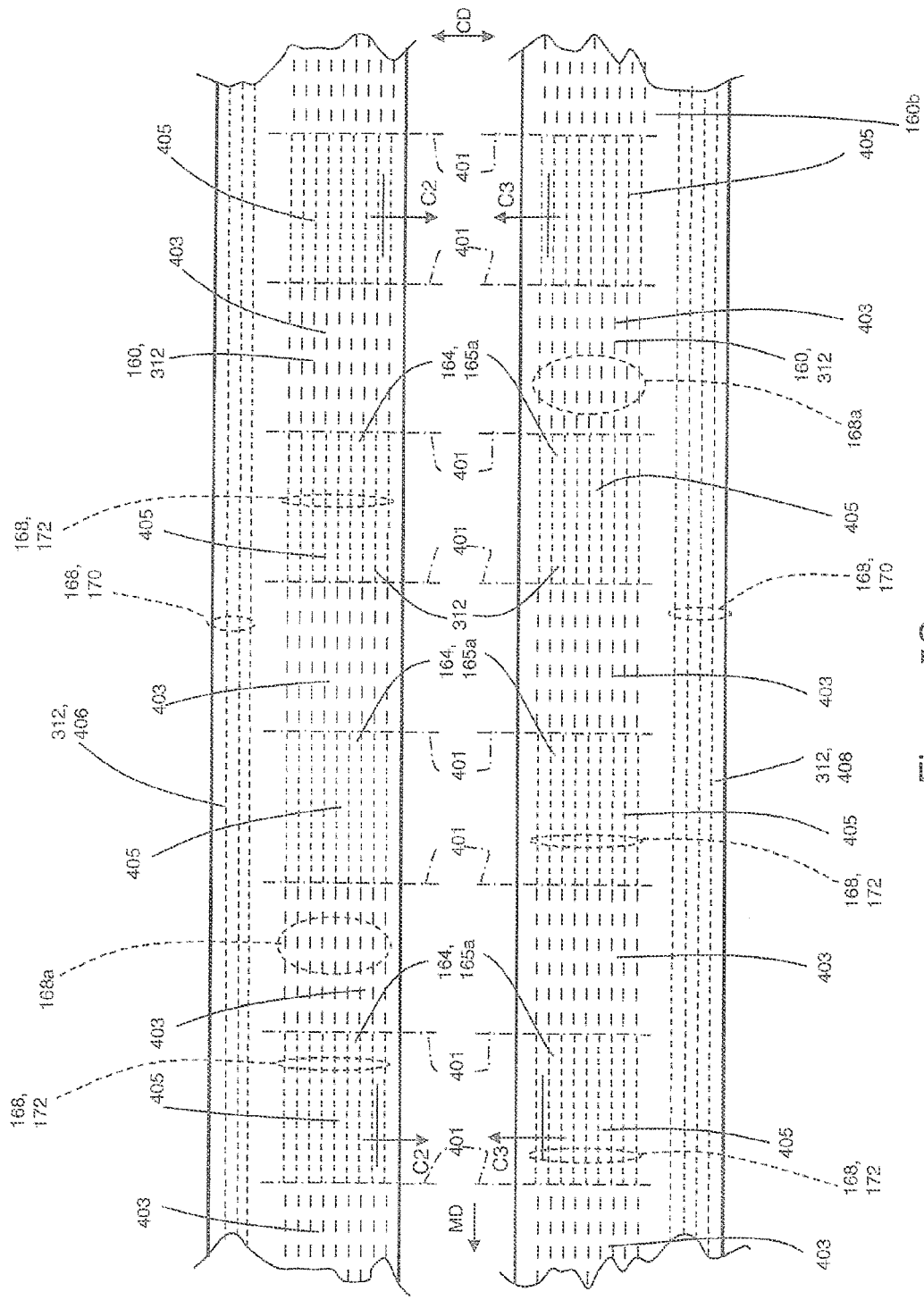
FIG. 5C is a view of continuous lengths of advancing first and second belt substrates material from FIG. 4 taken along line 5C-5C.

As shown in FIGS. 5C-5C4, the discrete pieces 168a of elastic material will remain in the light-bond regions 403. And the severed ends 404 of the discrete pieces of the inner elastics 172 will retract toward each other until the induced strain is substantially relieved as the belt substrates advance in the machine direction. In addition, the severed ends 404 of the inner elastics 172 will retract or snap back in a controlled fashion to the heavy-bond regions 405 of the first and second belt substrates 406, 408 as the belt substrates advance in the machine direction, and depending on the rate of retraction, may continue to retract once the assembled absorbent article has been packaged. As previously mentioned, although the inner elastics 172 are bonded to the outer layer belt material 162 or the inner layer belt material 164 by the substrate adhesive 504A in the light bond regions, the substrate adhesive 504A is not strong enough to hold the severed elastic ends 404 in a strained or stretched conditioned within the light bond regions 403. But the substrate adhesive 504A may be strong enough to hold the elastic pieces 168a in desired positions in the light-bond regions 403. At the same time, the substrate adhesive 504A allows the elastic pieces 168a to retract such that the cut elastics are deactivated in the light-bond regions.

It is to be appreciated that the substrate adhesive 504A and the elastic adhesive 504B may be applied in various ways and in various amounts depending on the particular application. For example, in some instances, the substrate adhesive 504A may be applied with a porous slot coat method. In some configurations, the substrate adhesive 504A may be applied in amounts ranging from 0.5 gsm to 10 gsm. It is to be appreciated that the adhesion strength (high versus low) can be varied in various ways. For example, in some embodiments, adhesion strength can be varied by the process techniques in which adhesive may be applied for a given type of adhesive. Some example application process techniques may include slot coating, meltblown, and spiral pattern applications. In some embodiments, adhesion strength can be varied by the basis weight in which adhesive is applied for a given type of adhesive. In some embodiments, adhesion strength can be varied by the type of adhesive that is applied, such as for example, a hot-melt adhesive sold under the product code PHO-3000 available from H.B. Fuller. In some embodiments, adhesion strength can be varied by the compression forces, such as with nonwoven substrates, wherein compression forces may affect how deep adhesives may be pressed into nonwoven fibers.

Figure 3:
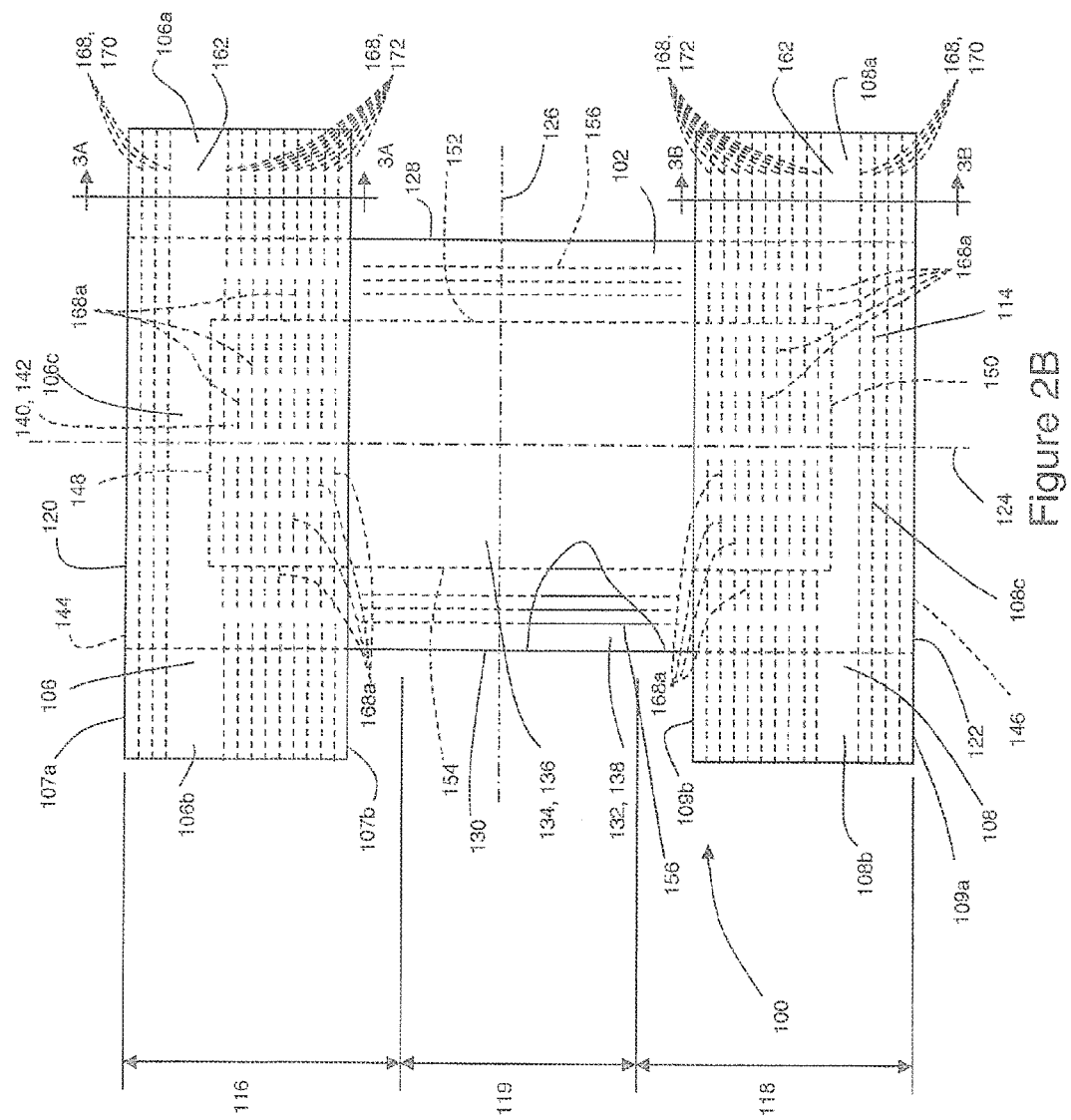

In some embodiments such as shown in FIGS. 5C2 and 5C3, the cutting unit 510 may be configured to sever only the elastics 168, 172 in the light-bond regions 403 of the first and/or second belt substrates 406, 408 without cutting through either the outer layer belt material 162 or the inner layer belt material 164. In other configurations, the cutting unit 510 may be configured to cut the elastics 168, 172 in the light-bond regions 403 of the first and second belt substrates 406, 408 while also cutting through one or both the outer layer belt material 162 and the inner layer belt material 164. For example, FIGS. 5C2A and 5C3A show a configuration where the cutting unit 510 cuts slits 413 through the inner layer belt material 164 while cutting the elastics 168, 172 in the light-bond regions 403 of the first and second belt substrates 406, 408, without cutting through the outer layer belt material 162. In another example, FIGS. 5C2B and 5C3B show a configuration where the cutting unit 510 cuts slits 413 through both the inner layer belt material 164 and the outer layer material 162 while cutting the elastics 168, 172 in the light-bond regions 403 of the first and second belt substrates 406, 408. Also, in some embodiments, such as shown in FIGS. 5C2B and 5C3B, the slits 413 in the outer layer material 162 may be offset or staggered relative to the slits 413 in the inner layer material 164 along the machine direction, as illustrated by the relative positions of center lines 413a of the slits 413.

As previously discussed, the inner elastic strands 172 are bonded to the outer layer belt material 162 and/or inner layer belt material 164 in the light-bond regions 403 with only the substrate adhesive 504A. However, it is to be appreciated that the light-bond regions 403 and heavy-bond regions 405 may be configured with various adhesive applications. For example, FIG. 5B3 shows a detailed view of a belt substrate 408 with the outer layer belt material 164 cut-away to illustrate an embodiment of adhesive application in the heavy-bond regions 405 and the light-bond regions 403. More particularly, FIG. 5B3 shows an example adhesive application configuration wherein substrate adhesive 504A has been applied to the belt materials 162, 164 and/or elastics 168, 170, 172 in the heavy-bond regions 405 and the light bond regions 403. In addition, elastic adhesive 504B has been applied either or both belt materials 162, 164, and/or the inner elastics 168, 172, in the heavy-bond regions 405, but not the light bond regions 403. As such, elastic adhesive 504B may be intermittently applied along the machine direction MD in the heavy-bond regions 405, and substrate adhesive 504A may be continuously applied along the machine direction in the light-bond regions 403 and the heavy-bond regions 405.

With continued reference to FIG. 5B3, elastic adhesive 504B may be applied to the elastics 168, 172 extending the machine direction MD in the heavy-bond regions 405. As such, the elastic adhesive 504B bonds the inner layer belt material 162, the outer layer belt material 164, and the elastics 168, 172 together in the heavy-bond regions 405. In addition, substrate adhesive 504A may be applied to one or more of the elastics 168, 172, the inner belt material 162, or the outer belt material 164 extending in the machine direction MD in the light-bond regions 403 and heavy-bond regions 405. As such, the substrate adhesive 504A bonds the inner layer belt material 162 and the outer layer belt material 164 together in the light-bond regions 403. As previously mentioned, the substrate adhesive 504A is not strong enough to hold the severed ends 404 of elastics 168, 172 in a prestrained or stretched state to either the inner layer belt material 162 or the outer layer belt material 164 in the light-bond regions 403 after having been cut. FIG. 5C3 shows a detailed view of the belt substrate 408 from FIG. 5B3 with the outer layer belt material 164 cut-away to illustrate the elastics 168, 172 after having been cut in the light-bond regions 403 wherein the severed ends 404 of the elastics 168, 172 have retracted or snapped back to the heavy-bond regions 405.

It is to be appreciated that various configurations of cutting units 510 can be used with the apparatuses and methods herein. Such cutting unit configurations may include features of the cutting knives/units disclosed, for example, in U.S. Pat. Nos. 5,393,360; 7,708,849; 7,861,756; 7,777,094; U.S. patent application Ser. No. 13/434,912, filed on Mar. 30, 2012; and U.S. Patent Application No. 61/617,713, filed on Mar. 30, 2012, which are all incorporated by reference herein. As such, the cutting units may be configured with die knife, flexible blade, and/or compression roll features, and may also include additional features to control knife-anvil gaps and/or force.

Figure 6:
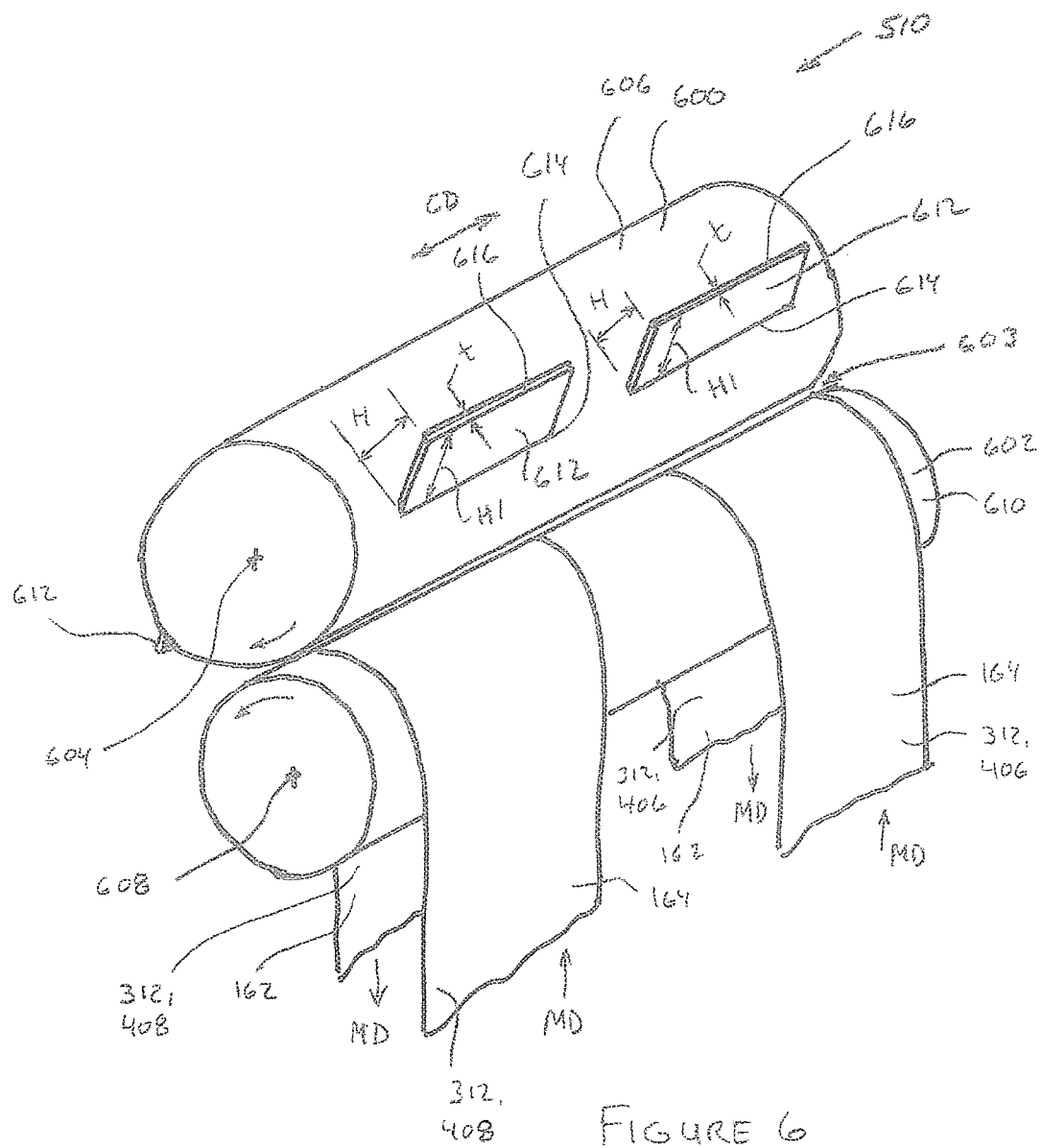
FIG. 6 is a perspective view of an embodiment of a cutting apparatus.
Figure 7:
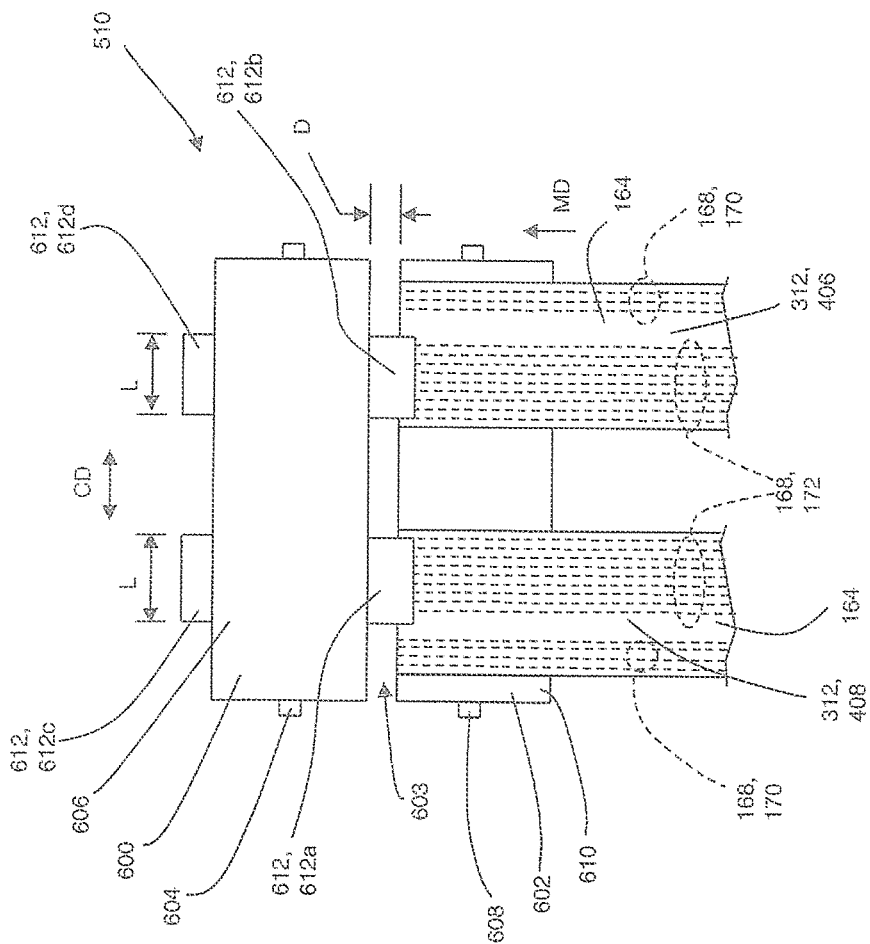
FIG. 7 is a front side view of the cutting apparatus of FIG. 6 as two blades are rotated toward two substrates partially wrapped around an anvil roll.

FIGS. 6 and 7 show an example embodiment of a cutting unit 510 including a cutting roll 600 and an anvil roll 602. The cutting roll 600 is adapted to rotate around an axis of rotation 604 and defines an outer circumferential surface 606. And the anvil roll 602 is adapted to rotate around an axis of rotation 608 and defines an outer circumferential surface 610. The cutting roll 600 is adjacent to the anvil roll 602 and create a nip 603 defined by a minimum distance, D, between the outer circumferential surface 606 of the cutting roll 602 and the outer circumferential surface 610 of the anvil roll 602. As shown in FIGS. 6 and 7, the cutting roll 600 may also include one or more blades 612. Each blade 612 may have a proximal end portion 614 extending in a cross direction (CD) a length, L, along the outer circumferential surface 606 of the cutting roll 600. The blades 612 may define a dimension, H1, extending from the proximal end portion 614 to a distal edge 616. In addition, from the proximal end portion 614, the blades may extend radially outward from the outer circumferential surface 606 of the cutting roll 600 to the distal edge 616 by a distance, H. It is to be appreciated that the blades 612 may extend radially outward from the outer circumferential surface 606 to define an angle of 90 degrees or less, such as about 45 degrees, between the blade 612 and a tangential plane intersecting the proximal end portion 614 on the outer circumferential surface 606. As such, in some embodiments, H1 may be equal to H, and in some embodiments, H1 may be greater than H. As shown in FIGS. 6 and 7, the blades 612 may define a rectangular shape having a first surface 618 and an opposing second surface 620 separated by a thickness, t. The blades 612 may have a small thickness, t, relative to the distance, H1, such that blades 612 are flexible or bendable.

As shown in FIGS. 6-8C, the cutting unit 510 may be arranged such that the first and second belt substrates 406, 408 advance in a machine direction MD to partially wrap around the outer circumferential surface 610 of the anvil roll 602. As the anvil roll 602 and the cutting roll 600 rotate, portions of the first surfaces 618 and the distal edges 616 of the blades 612 are moved into contact with the first and second belt substrates 406, 408, such as shown in FIG. 8A. As shown in FIGS. 8A-8C, the distance, H, of each blade 612 is greater than the distance, D, between the cutting roll 600 and the anvil roll 602. Thus, with reference to FIG. 8B, as the blades 612 rotate though the nip 603 between the cutting roll 600 and the anvil roll 602, the blades 612 flex or bend inward along the second surface 620. As such, portions of the first surfaces 618 and/or the distal edges 616 of the blades 612 exert pressure on the first and second belt substrates 406, 408 to cut the elastics 168, 172 in the light-bond regions 403. Referring now to FIG. 8C, as the cutting roll 600 continues to rotate, the blades 612 move away from the nip 603 and straighten back out along the distance, H1, thus returning to the original blade shapes before entering the nip 603.

It is to be appreciated that the belt substrate materials may be arranged in various ways on the cutting unit 510. For example, as shown in FIGS. 6-8C, the front belt substrate material 406 and the back belt substrate material 408 may advance in the machine direction MD to partially wrap around the rotating anvil roll 602 such that the outer layer belt material 162 of the front belt substrate material 406 and the back belt substrate material 408 are in contact with the outer circumferential surface 610 of the anvil roll 602. As such, the blades 612 of the rotating cutting roll 600 contact the inner layer belt material 164 of the front belt substrate material 406 and the back belt substrate material 408 while advancing through the nip 603. It is to be appreciated that the front and back belt substrates 406, 408 may be arranged such that either the inner layer of belt material 162 or the outer layer of belt material 164 is in contact with the outer circumferential surface 610 of the anvil roll 602. For example, in some embodiments, the front belt substrate material 406 and the back belt substrate material 408 may be arranged to partially wrap around the rotating anvil roll 602 such that the inner layer of belt material 162 of the front belt substrate material 406 and the back belt substrate material 408 are in contact with the outer circumferential surface 610 of the anvil roll 602. As discussed above, the cutting unit 510 shown in FIGS. 6-8C may be configured to sever only the elastics 168, 172 in the light-bond regions 403 of the first and/or second belt substrates 406, 408 without cutting through either the outer layer belt material 162 or the inner layer belt material 164. In other configurations, the cutting unit 510 may be configured to cut the elastics 168, 172 in the light-bond regions 403 of the first and second belt substrates 406, 408 while also cutting through one or both the outer layer belt material 162 and the inner layer belt material 164.

It is to be appreciated that the cutting unit 510 may be configured with various quantities of blades having various shapes and orientations. For example, the cutting unit 510 shown in FIGS. 6-8C includes four blades 612a, 612b, 612c, 612d. The first and second blades 612a, 612b may be located 180 degrees apart from the third and fourth blades 612c, 612d on the outer circumferential surface 606 of the cutting roll 600. It is to be appreciated that the cutting roll may also be configured with various numbers of blades arranged circumferentially along the outer circumferential surface 606 of the cutting roll 600. The proximal end portions 614 of the first blade 612a and the second blade 612b may also be aligned with each other and with the axis of rotation 604 so as to extend in a straight line in the cross direction (CD) perpendicular to the machine direction (MD). Similarly, proximal end portions 614 of the third blade 612c and the fourth blade 612d may be aligned with each other and with the axis of rotation 604 so as to extend in a straight line in the cross direction (CD) perpendicular to the machine direction (MD). In addition, the first blade 612a and the second blade 612b, as well as the third and fourth blades 612c, 612d, may define different lengths, L, and may separated from each other by various distances in the cross direction CD. For example, the lengths, L, of the blades 612 are configured such so as to engage portions of the first and second belt substrates 406, 408 so as to cut the elastics 168, 172 without cutting elastics 168, 170. In addition, the blades 612 may be configured to cut the elastics 168, 172 simultaneously in the CD direction along in a substantially straight line. It is also to be appreciated that the cutting roll 600 may be configured with more than or less than two blades 612 aligned along the CD direction of outer circumferential surface 606 of the cutting roll 600. For example, in some embodiments, instead of having the first blade 612a and the second blade 612b, the cutting roll 600 may be configured with a single blade 612 extending along the CD direction for a length, L, on the outer circumferential surface 606. It is also to be appreciated that the cutting roll 600 may be configured to cut the elastics more than once in a zone or region. For example, the cutting roll 600 may be configured to cut the elastics 168, 172 more than once in a light-bond region 403.

Referring back to FIG. 4, from the cutting unit 510, the first and second belt substrates 406, 408 advance in the machine direction MD and are combined with discrete chassis 102. As shown in FIGS. 4 and 5D, a continuous length of chassis assemblies 302 are advanced in a machine direction MD to a carrier apparatus 512 and cut into discrete chassis 102 with knife roll 514. As shown in FIG. 5D, the continuous length of chassis assemblies 302 may include absorbent assemblies 140 sandwiched between topsheet material 138 and backsheet material 136, leg elastics, barrier leg cuffs and the like. A portion of the chassis assembly is cut-away to show a portion of the topsheet material 138 and an absorbent assembly 140.

After the continuous web of absorbent chassis 102 are cut by the knife roll 514, the carrier apparatus 512 rotates and advances the discrete chassis 102 in the machine direction MD in the orientation shown in FIG. 5E1, wherein the longitudinal axis 124 of the chassis 102 is rotated from generally parallel with the machine direction MD to a position that is generally perpendicular to the machine direction. While the chassis 102 shown in FIG. 5E1 is shown with the second laterally extending end edge 146 as a leading edge and the first laterally extending end edge 144 as the trailing edge, it is to be appreciated that in other embodiments, the chassis 102 may be advanced in other orientations. For example, the chassis may be oriented such that the second laterally extending end edge 146 is a trailing edge and the first laterally extending end edge 144 is a leading edge. The carrier apparatus 308 also rotates while at the same time changing the orientation of the advancing chassis 102. The carrier apparatus 308 may also change the speed at which the chassis 102 advances in the machine direction MD. It is to be appreciated that various forms of carrier apparatuses may be used with the methods herein, such as for example, the carrier apparatuses disclosed in U.S. Pat. No. 7,587,966. FIG. 5E2 shows an orientation of the chassis 102 on the carrier apparatus 308 while advancing in the machine direction that is different from that depicted in FIG. 5E1. More particularly, FIG. 5E2 shows the chassis 102 with the lateral axis 126 of the chassis 102 generally parallel with the machine direction MD, and wherein the first longitudinal side edge 128 is the leading edge and the second longitudinal side edge 130 is the trailing edge.

As discussed below with reference to FIGS. 4, 5F, 5G, and 5H, the chassis 102 are transferred from the carrier apparatus 512 and combined with advancing, continuous lengths of belt substrates 406, 408, which are subsequently cut to form first and second elastic belts 106, 108 on diapers 100.

Figure 5F:
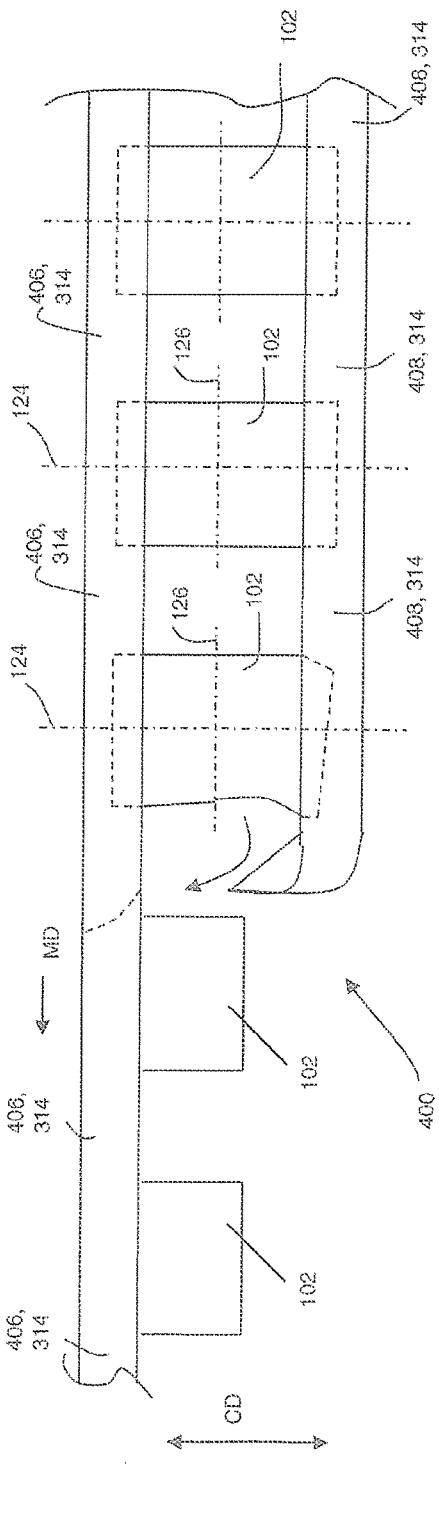
FIG. 5F is a view of multiple discrete chassis spaced from each other along the machine direction MD and connected with each other by the front and back side panel material from FIG. 4 taken along line 5F-5F.

With reference to FIGS. 4 and 5F, the chassis 102 are transferred from the carrier apparatus 512 to a nip 516 between the carrier apparatus 512 and a roll 518 where the chassis 102 are combined with continuous lengths of advancing front belt substrate material 406 and back belt substrate material 408. The front belt substrate material 406 and the back belt substrate material 408 each define a wearer facing surface 312 and an opposing garment facing surface 314. The wearer facing surface 312 of the first belt substrate 406 may be combined with the garment facing surface 134 of the chassis 102 along the first waist region 116, and the wearer facing surface 312 of the second belt substrate 408 may be combined with the garment facing surface 134 of the chassis 102 along the second waist region 118. As shown in FIG. 4, adhesive 520 may be intermittently applied to the wearer facing surface 312 of the first and second belt substrates 406, 408 before combining with the discrete chassis 102 at the nip 516 between roll 518 and the carrier apparatus 512. In some embodiments, the chassis 102 may be joined to the first and second belts in various different ways, such as for example, thermal bonds, pressure bonds, ultrasonic bonds, adhesives and combinations thereof.

In some embodiments, such as shown in FIGS. 4, 5C, 5C1, 5C2, and 5F, adhesive 520 may be intermittently applied to portions of the body facing surface 312 at the light-bond regions 403 of the first belt substrate 406 and/or the second belt substrate 408. And adhesive may not be applied to portions of the body facing surface 312 at the heavy-bond regions 405 of the first belt substrate 406 and/or the second belt substrate 408. As such, the garment facing surface 134 of the chassis 102 may be combined in an overlapping relationship with the light-bond regions 403 of the first belt substrate 406 and/or the second belt substrate 408. As such, in some embodiments, the light-bond regions 403 of the first and second belt substrates 406, 408 may correspond with and/or define the central regions 106c, 108c of the first and second elastic belts 106, 108 discussed above with reference to FIGS. 1-2B. In addition, the heavy-bond regions 405 may correspond with and/or define the opposing end regions 106a, 106b, 108a, 108b of the of the first and second elastic belts 106, 108 discussed above with reference to FIGS. 1-2B.

As mentioned above, the converting process can be configured in various ways such that the severed elastic ends retract within the light-bond regions at a controlled rate dictated in part by the basis weight and/or type of substrate adhesive applied in the light-bond regions. As such, in some embodiments, the chassis 102 can be placed on the light-bond regions 403 before the severed elastics 168, 172 have fully retracted. In some embodiments, the chassis 102 can be placed on the light-bond regions 403 after the severed elastics 168, 172 have fully retracted. It should also be appreciated that the heavy-bond regions 405 and light-bond regions 403 may have various sizes relative to the chassis 102. For example, in some embodiments, portions of the chassis 102 may overlap or may be positioned on top of the severed ends 404 and/or portions of the severed elastics 168, 172. In some embodiments, the severed ends 404 of the elastics 168, 172 may be aligned with or may be outside of the longitudinal edges 128, 130 of the chassis 102. In some embodiments, the severed elastics may not be fully retracted until positioned within an assembled absorbent article placed within a package.

Figure 5G:
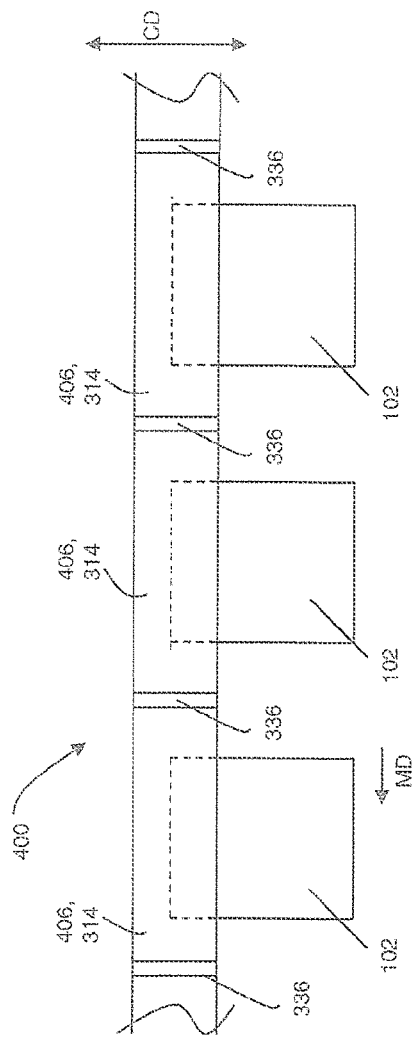
FIG. 5G is a view of folded multiple discrete chassis with the front and back side panel material in a facing relationship from FIG. 4 taken along line 5G-5G.

With reference to FIGS. 4 and 5F, a continuous length of absorbent articles 400 are defined by multiple discrete chassis 102 spaced from each other along the machine direction MD and connected with each other by the second belt substrate 408 and the first belt substrate 406. As shown in FIG. 4, the continuous length of absorbent articles 400 advances from the nip 516 to a folding apparatus 522. At the folding apparatus 522, each chassis 102 is folded in the cross direction CD along a lateral axis 126 to place the first waist region 116, and specifically, the inner, body facing surface 132 into a facing, surface to surface orientation with the inner, body surface 132 of the second waist region 118. The folding of the chassis also positions the wearer facing surface 312 of the second belt substrate 408 extending between each chassis 102 in a facing relationship with the wearer facing surface 312 of the first belt substrate 406 extending between each chassis 102. As shown in FIGS. 4, 5F, and 5G, the folded discrete chassis 102 connected with the first and second belt substrates 406, 408 are advanced from the folding apparatus 522 to a bonder 524. The bonder 524 operates to bond a portion of the second belt substrate 408 extending between each chassis 102 with a portion of the first belt substrate 406 extending between each chassis 102, thus creating discrete bond regions 336. It is to be appreciated that various types of bonder apparatuses and methods can be used to bond the second belt substrate material 408 with the first belt substrate material 406, such as for example disclosed in U.S. Pat. Nos. 6,248,195; 6,546,987; and 7,383,865, as well as U.S. Patent Publication No. 2012/0021186A1, which are incorporated by reference herein.

As shown in FIGS. 4 and 5H, a continuous length of absorbent articles are advanced from the bonder 524 to a knife roll 526 where the discrete bond regions 336 are cut along the cross direction to create a first side seam 178 on an absorbent article 100 and a second side seam 180 on a subsequently advancing absorbent article.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling disposable diapers, each diaper comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprising the steps of:

advancing a first continuous substrate layer having a first surface and an opposing second surface in a machine direction, and defining a width in a cross direction;

advancing a second continuous substrate layer having a first surface and an opposing second surface in a machine direction, and defining a width in a cross direction;

applying a first adhesive continuously along the machine direction to the first surface of the first continuous substrate layer;

advancing elastic strands in the machine direction in a stretched state;

applying a second adhesive intermittently along the machine direction to at least one of the elastic strands, the first surface of the first continuous substrate layer, and the first surface of the second continuous substrate layer;

bonding the elastic strands in the stretched state directly to the first surface of the first substrate layer and directly to the first surface of the second substrate layer to form an elastic laminate, the elastic laminate including first regions that include the first adhesive and not the second adhesive, and second regions including both the first adhesive and the second adhesive, the second regions intermittently spaced along the machine direction;

cutting the elastic laminate along the machine direction to form a first continuous elastic laminate and a second continuous elastic laminate, each of the first continuous elastic laminate and the second continuous elastic laminate including first regions and second regions;

separating the first continuous elastic laminate and the second elastic laminate in the cross direction;

severing elastic strands into one or more discrete lengths in the first regions of the first continuous elastic laminate and the second elastic laminate, wherein ends of the severed elastic strands retract from the first regions to the second regions, and wherein severing the elastic strands further comprises cutting the first slits in the first continuous substrate layer in the first regions and cutting second slits in the second continuous substrate layer in the first regions, wherein the first slits are offset from the second slits in the machine direction; and bonding the first end regions of each chassis with first regions of first continuous elastic laminate, and bonding the second end regions of each chassis with first regions of the second continuous elastic laminate.

2. The method of claim 1, wherein the step of severing the elastic strands further comprises cutting the elastic strands and the first continuous substrate layer in the first regions without cutting the second continuous substrate layer.

3. The method of claim 1, further comprising the steps of:
advancing a third continuous web in the machine direction;
cutting the third continuous web into discrete chassis, wherein each chassis advances such that the longitudinal axis is parallel with the machine direction; and
turning each chassis such that the lateral axis is parallel with the machine direction.

4. The method of claim 3 further comprising the steps of:
folding each chassis along the lateral axis to position the first continuous elastic laminate into a facing relationship with the second continuous elastic laminate;
bonding the first continuous elastic laminate with the second continuous elastic laminate at discrete bond regions; and
cutting the first and second continuous elastic laminates to form diaper side seams.

5. The method of claim 1, wherein the first end region is a front waist region.

6. The method of claim 1, wherein the second end region is a back waist region.

* * * * *